(12) United States Patent
Khattak et al.

(10) Patent No.: US 9,789,483 B2
(45) Date of Patent: Oct. 17, 2017

(54) SYSTEM FOR PORTABLE AND EASY-TO-USE DETECTION OF ANALYTES WITH MOBILE COMPUTING DEVICE

(71) Applicant: Cue Inc., San Diego, CA (US)

(72) Inventors: Ayub Khattak, San Diego, CA (US); Clinton Sever, San Diego, CA (US)

(73) Assignee: CUE INC., San Diego, CA (US)

( * ) Notice: Subject to any disclaimer, the term of this patent is extended or adjusted under 35 U.S.C. 154(b) by 0 days.

(21) Appl. No.: 14/205,146

(22) Filed: Mar. 11, 2014

(65) Prior Publication Data

US 2014/0336083 A1  Nov. 13, 2014

Related U.S. Application Data

(60) Provisional application No. 61/776,254, filed on Mar. 11, 2013.

(51) Int. Cl.
*G01N 33/00* (2006.01)
*B01L 3/00* (2006.01)
(Continued)

(52) U.S. Cl.
CPC ....... *B01L 3/502715* (2013.01); *B01L 3/5027* (2013.01); *B01L 3/502723* (2013.01); *B01L 3/502738* (2013.01); *B05D 3/002* (2013.01); *C12Q 1/6825* (2013.01); *F16K 99/0032* (2013.01); *F16K 99/0036* (2013.01); *G01N 27/28* (2013.01); *G01N 27/3271* (2013.01); *G01N 27/3273* (2013.01); *G01N 33/5438* (2013.01); *G01N 33/54306* (2013.01); *G01N 33/54326* (2013.01); *G01N 33/54333* (2013.01); *G01N 33/54366* (2013.01); *G01N 33/54373* (2013.01); *G01N 33/581* (2013.01); *G01N 35/00029* (2013.01); *G01N 35/0098* (2013.01); *G01N 35/08* (2013.01); *H04M 1/72527* (2013.01); *B01L 3/5029* (2013.01);
(Continued)

(58) Field of Classification Search
CPC ....... G01N 33/581; G01N 1/02; B01L 3/5029
See application file for complete search history.

(56) References Cited

U.S. PATENT DOCUMENTS

| 3,915,806 | A | 10/1975 | Horlach |
| D298,166 | S | 10/1988 | Chennault |

(Continued)

FOREIGN PATENT DOCUMENTS

| EP | 2 050 498 A1 | 4/2009 |
| EP | 2 179 294 A2 | 4/2010 |

(Continued)

OTHER PUBLICATIONS

U.S. Appl. No. 14/479,149, filed Sep. 5, 2014, Cue, Inc.
(Continued)

*Primary Examiner* — Sam P Siefke
(74) *Attorney, Agent, or Firm* — Foley & Lardner LLP; Antoinette F. Konski; Christopher C. Bolten

(57) ABSTRACT

This system takes in raw cellular material collected using a provided swab, blood collection device, urine collection device, or other sample collection device and transforms that biological material into a digital result, identifying the presence, absence and/or quantity of nucleic acids, proteins, and/or other molecules of interest.

17 Claims, 26 Drawing Sheets

(51) Int. Cl.
| | |
|---|---|
| *G01N 35/08* | (2006.01) |
| *G01N 33/543* | (2006.01) |
| *H04M 1/725* | (2006.01) |
| *G01N 35/00* | (2006.01) |
| *G01N 27/28* | (2006.01) |
| *B05D 3/00* | (2006.01) |
| *F16K 99/00* | (2006.01) |
| *C12Q 1/68* | (2006.01) |
| *G01N 33/58* | (2006.01) |
| *G01N 1/02* | (2006.01) |
| *G01N 35/10* | (2006.01) |
| *G01N 21/78* | (2006.01) |
| *G01N 27/327* | (2006.01) |

(52) U.S. Cl.
CPC ... *B01L 2200/025* (2013.01); *B01L 2200/026* (2013.01); *B01L 2200/027* (2013.01); *B01L 2200/028* (2013.01); *B01L 2200/0668* (2013.01); *B01L 2200/0684* (2013.01); *B01L 2200/0689* (2013.01); *B01L 2200/087* (2013.01); *B01L 2200/10* (2013.01); *B01L 2200/16* (2013.01); *B01L 2300/023* (2013.01); *B01L 2300/025* (2013.01); *B01L 2300/04* (2013.01); *B01L 2300/044* (2013.01); *B01L 2300/06* (2013.01); *B01L 2300/0627* (2013.01); *B01L 2300/0645* (2013.01); *B01L 2300/0681* (2013.01); *B01L 2300/087* (2013.01); *B01L 2300/0816* (2013.01); *B01L 2300/0838* (2013.01); *B01L 2300/0864* (2013.01); *B01L 2300/0867* (2013.01); *B01L 2300/12* (2013.01); *B01L 2300/161* (2013.01); *B01L 2300/1827* (2013.01); *B01L 2400/0406* (2013.01); *B01L 2400/0487* (2013.01); *B01L 2400/0677* (2013.01); *B01L 2400/0683* (2013.01); *B05D 2518/00* (2013.01); *F16K 2099/0084* (2013.01); *G01N 1/02* (2013.01); *G01N 21/78* (2013.01); *G01N 27/3272* (2013.01); *G01N 35/1095* (2013.01); *G01N 2001/027* (2013.01); *G01N 2001/028* (2013.01); *G01N 2035/00277* (2013.01); *G01N 2035/00564* (2013.01); *G01N 2458/30* (2013.01); *H04M 1/7253* (2013.01); *Y10T 137/1797* (2013.01)

(56) References Cited

U.S. PATENT DOCUMENTS

| | | | |
|---|---|---|---|
| D302,585 S | 8/1989 | Elliott | |
| 5,708,247 A | 1/1998 | McAleer et al. | |
| 5,935,804 A | 8/1999 | Laine et al. | |
| 6,523,560 B1 | 2/2003 | Williams et al. | |
| D472,975 S | 4/2003 | Iori et al. | |
| 6,893,879 B2 | 5/2005 | Petersen et al. | |
| 7,118,667 B2 | 10/2006 | Lee | |
| 7,195,036 B2 | 3/2007 | Burns et al. | |
| D542,931 S | 5/2007 | Pukall et al. | |
| 7,285,412 B2 | 10/2007 | Casagrande et al. | |
| 7,291,497 B2 | 11/2007 | Holmes et al. | |
| 7,432,106 B2 | 10/2008 | Cox | |
| 7,478,792 B2 | 1/2009 | Oh et al. | |
| D591,864 S | 5/2009 | Schmidt | |
| D600,578 S | 9/2009 | Tsuji | |
| 7,635,594 B2 | 12/2009 | Holmes et al. | |
| 7,723,099 B2 | 5/2010 | Miller et al. | |
| 7,888,125 B2 | 2/2011 | Gibbons et al. | |
| 7,981,696 B2 | 7/2011 | Moreland et al. | |
| 8,007,999 B2 | 8/2011 | Holmes et al. | |
| 8,008,034 B2 | 8/2011 | Gibbons et al. | |
| 8,012,744 B2 | 9/2011 | Gibbons et al. | |
| D646,189 S | 10/2011 | Dinter et al. | |
| 8,071,054 B2 | 12/2011 | Oh et al. | |
| 8,101,402 B2 | 1/2012 | Holmes | |
| 8,202,697 B2 | 6/2012 | Holmes | |
| 8,216,832 B2 | 7/2012 | Battrell et al. | |
| 8,265,955 B2 | 9/2012 | Michelson et al. | |
| 8,283,155 B2 | 10/2012 | Holmes et al. | |
| 8,361,808 B2 | 1/2013 | Wang | |
| D679,025 S | 3/2013 | Motadel et al. | |
| 8,435,738 B2 | 5/2013 | Holmes | |
| 8,449,842 B2 | 5/2013 | Knopp et al. | |
| 8,470,524 B2 | 6/2013 | Gibbons et al. | |
| 8,475,739 B2 | 7/2013 | Holmes et al. | |
| 8,551,714 B2 | 10/2013 | Jovanovich et al. | |
| 8,562,918 B2 | 10/2013 | Jovanovich et al. | |
| 8,669,047 B2 | 3/2014 | Holmes et al. | |
| 8,679,407 B2 | 3/2014 | Holmes et al. | |
| 8,724,833 B1 | 5/2014 | Shain et al. | |
| D707,847 S | 6/2014 | Motadel et al. | |
| 8,741,230 B2 | 6/2014 | Holmes et al. | |
| 8,778,665 B2 | 7/2014 | Gibbons et al. | |
| D718,462 S | 11/2014 | Cook et al. | |
| D719,666 S | 12/2014 | Manian | |
| D745,185 S | 12/2015 | Kimura et al. | |
| 9,310,231 B2 | 4/2016 | Bloss et al. | |
| 2002/0002326 A1* | 1/2002 | Causey et al. | 600/300 |
| 2002/0137234 A1 | 9/2002 | Wohlstadter et al. | |
| 2003/0019522 A1 | 1/2003 | Parunak | |
| 2004/0082878 A1 | 4/2004 | Baldwin et al. | |
| 2004/0173456 A1 | 9/2004 | Boos et al. | |
| 2004/0189311 A1 | 9/2004 | Glezer et al. | |
| 2004/0219732 A1* | 11/2004 | Burns | F16K 99/0015 438/200 |
| 2005/0136529 A1 | 6/2005 | Yang et al. | |
| 2005/0171528 A1 | 8/2005 | Sartor et al. | |
| 2005/0178700 A1 | 8/2005 | Tyvoll et al. | |
| 2005/0200643 A1 | 9/2005 | Falcon | |
| 2006/0131994 A1 | 6/2006 | D'Angelico et al. | |
| 2006/0160205 A1 | 7/2006 | Blackburn et al. | |
| 2006/0207891 A1 | 9/2006 | Althaus et al. | |
| 2006/0243591 A1 | 11/2006 | Plotkin et al. | |
| 2007/0031283 A1* | 2/2007 | Davis | A61B 5/14546 422/400 |
| 2007/0154922 A1 | 7/2007 | Collier et al. | |
| 2007/0184547 A1 | 8/2007 | Handique et al. | |
| 2008/0124779 A1 | 5/2008 | Oh et al. | |
| 2008/0160601 A1 | 7/2008 | Handique | |
| 2008/0160622 A1 | 7/2008 | Su et al. | |
| 2008/0160630 A1 | 7/2008 | Liu et al. | |
| 2008/0182301 A1 | 7/2008 | Handique et al. | |
| 2008/0302193 A1 | 12/2008 | Bommarito et al. | |
| 2009/0061450 A1 | 3/2009 | Hunter | |
| 2010/0236340 A1 | 9/2010 | Lee et al. | |
| 2010/0274155 A1 | 10/2010 | Battrell et al. | |
| 2010/0297708 A1 | 11/2010 | Collier et al. | |
| 2010/0331652 A1* | 12/2010 | Groll et al. | 600/365 |
| 2011/0008813 A1 | 1/2011 | Dilleen et al. | |
| 2011/0059468 A1 | 3/2011 | Earhart et al. | |
| 2011/0129841 A1 | 6/2011 | Heid et al. | |
| 2011/0165562 A1 | 7/2011 | Pourahmadi et al. | |
| 2011/0171754 A1 | 7/2011 | Redmond et al. | |
| 2011/0212440 A1 | 9/2011 | Viovy et al. | |
| 2011/0272294 A1 | 11/2011 | Fujiwara | |
| 2012/0009588 A1 | 1/2012 | Rajagopal et al. | |
| 2012/0014836 A1 | 1/2012 | Dittmer | |
| 2012/0071342 A1 | 3/2012 | Lochhead et al. | |
| 2012/0095316 A1 | 4/2012 | Lewis et al. | |
| 2012/0164036 A1 | 6/2012 | Stern et al. | |
| 2012/0180580 A1 | 7/2012 | Immink et al. | |
| 2012/0190589 A1 | 7/2012 | Anderson et al. | |
| 2012/0255860 A1 | 10/2012 | Briman et al. | |
| 2012/0267258 A1 | 10/2012 | Uraoka et al. | |
| 2012/0271127 A1 | 10/2012 | Battrell et al. | |
| 2013/0011210 A1 | 1/2013 | Toner et al. | |
| 2013/0029324 A1 | 1/2013 | Rajagopal et al. | |
| 2013/0085680 A1 | 4/2013 | Arlen et al. | |
| 2013/0137591 A1 | 5/2013 | Clemens et al. | |
| 2013/0244339 A1 | 9/2013 | Ehrenkranz et al. | |
| 2013/0273528 A1 | 10/2013 | Ehrenkranz | |

(56) References Cited

U.S. PATENT DOCUMENTS

| | | |
|---|---|---|
| 2013/0309778 A1 | 11/2013 | Lowe et al. |
| 2014/0027286 A1 | 1/2014 | Ikegami et al. |
| 2014/0030717 A1 | 1/2014 | Zhong et al. |
| 2014/0194305 A1 | 7/2014 | Kayyem et al. |
| 2016/0091518 A1 | 3/2016 | Khattak et al. |
| 2017/0043334 A1 | 2/2017 | Khattak et al. |
| 2017/0043335 A1 | 2/2017 | Khattak et al. |
| 2017/0043336 A1 | 2/2017 | Khattak et al. |
| 2017/0043342 A1 | 2/2017 | Khattak et al. |
| 2017/0045507 A1 | 2/2017 | Khattak et al. |
| 2017/0045508 A1 | 2/2017 | Khattak et al. |

FOREIGN PATENT DOCUMENTS

| | | |
|---|---|---|
| GB | 2 430 032 A | 3/2007 |
| JP | 2007-505319 | 3/2007 |
| JP | 2009-531064 | 9/2009 |
| JP | 2012-504956 | 3/2012 |
| JP | 2012-528995 | 11/2012 |
| WO | WO-2005/026689 | 3/2005 |
| WO | WO-2007/112114 A2 | 10/2007 |
| WO | WO-2010/036808 A1 | 4/2010 |
| WO | WO-2010/041231 | 4/2010 |
| WO | WO-2010/140128 | 12/2010 |
| WO | WO-2012/170703 A1 | 12/2012 |
| WO | WO-2013/136115 A1 | 9/2013 |
| WO | WO-2013/144643 A2 | 10/2013 |
| WO | WO 2016/040642 | 3/2016 |

OTHER PUBLICATIONS

U.S. Appl. No. 14/543,842, filed Nov. 17, 2014, Cue Inc.
U.S. Appl. No. 29/490,660, filed May 12, 2014, Cue Inc.
Anderson, J.C. et al. (2008) "Thermally-Actuated Microfluidic Syitems," J. Assoc. Laboratory Automation 13:65-72.
Beyor, N. et al. (2008) "Immunomagnetic Bead-Based Cell Concentration Microdevice for Dilute Pathogen Detection," Biomed Microdevices 10:909-917.
Chen, Z. et al. (2005) "Thermally-Actuated, Phase Change Flow Control for Microfuidic Systems," Lab Chip 5:1277-1285.
Cho, H. et al. (2007) "How the Capillary Burst Microvalve Works," J. of Colloid and Interface Science 306:379-385.
Clinical IVD Products: Liat™ Analyzer; IQuum, Inc.: http://www.iquum.com/products/analyzer.shtml. Last Accessed May 5, 2014.
Fan, R. et al. (2008) "Integrated Barcode Chips for Rapid, Multiplexed Analysis of Proteins in Microliter Quantities of Blood," Nature Biotechnology 26(12)1373-1378.
Ferguson, B.S. et al. (2009) "Integrated Microfluidic Electrochemical DNA Sensor," Analytical Chemistry 81(15):6503-6508.
Henares, T.G. et al. (2007) "Integration of Multianalyte Sensing Functions on a Capillary-Assembled Microchip: Simultaneous Determination of Ion Concentration and Enzymatic Activities by a 'Drop-and-Sip' Technique," Analytical Chemistry 79(3):908-915.
International Search Report and Written Opinion of the International Search Authority for International Application No. PCT/US2014/023821, dated Jul. 7, 2014, 12 pages.
Jagannathan, H. et al. (2001) "Micro-Fluidic Channels with Integrated Ultrasonic Transducers," IEEE Ultrasonics Symposium 2001:859-862.
Kaigala, G.V. et al. (2008) "Electrically Controlled Microvalves to Integrate Microchip Chip Polymerase Chain Reaction and Capillary Electrophoresis," Lab Chip 8:1071-1078.
Kim, D. et al. (2007) "A Bi-Polymer Micro One-Way Valve," Sensors and Actuators A 136:426-433.
Kinoshita, T. et al. (2007) "Functionalization of Magnetic Gold/Iron-Oxide Composite Nanoparticles with Oligonucleotides and Magnetic Separation of Specific Target," J. of Magnetism and Magnetic Materials 311:255-258.
Kwakye, S. et al. (2006) "Electrochemical Microfluidic Biosensor for Nucleic Acid Detection with Integrated Minipotentiostat," Biosensors and Bioelectronics 21:2217-2223.

Laschi, S. et al. (2010) "A New Gravity-Driven Microfluidic-Based Electrochemical Assay Coupled to Magnetic Beads for Nucleic Acid Detection," Electrophoresis 31:3727-3736.
Lawi, W. et al. (2009) "A Microfluidic Cartridge System for Multiplexed Clinical Analysis," J. Assoc. Laboratory Automation 14(6):407-412.
Lee, C.S. et al. (2001) "Microelectromagnets for the Control of Magnetic Nanoparticles," Applied Physics Letters 79(20):3308-3310.
Lillehoj, P.B. et al. (2010) "A Self-Pumping Lab-on-a-Chip for Rapid Detection of Botulinum Toxin," Lab Chip 10:2265-2270.
Liu, R.H. et al. (2004) "Single-use, Thermally Actuated Parafin Valves for Microfluidic Applications," Sensors and Actuators B 98:328-336.
Liu, R.H. et al. (2004) "Self-Contained, Fully Integrated Biochip for Sample Preparation, Polymerase Chain Reaction Amplification, and DNA Microarray Detection," Analytical Chemistry 76(7):1824-1831.
Marentis, T.C. et al. (2005) "Microfluidic Sonicator for Real-Time Disruption of Eukaryotic Cells and Bacterial Spores for DNA Analysis," Ultrasound in Med. & Biol. 31(9):1265-1277.
Mrksich, M. et al. (1997) "Using Self-Assembled Monolayers that Present Oligo(ethylene glycol) Groups to Control the Interactions of Proteins with Surfaces," American Chemical Society Symposium Series 680:361-373.
Rida, A. et al. (2004) "Manipulation of Self-Assembled Structures of Magnetic Beads for Microfluidic Mixing and Assaying," Analytical Chemistry 76(21):6239-6246.
Rodaree, K. et al. (2011) "DNA Hybridization Enhancement Using Piezoelectric Microagitation through a Liquid Coupling Medium," Lab Chip; doi:10.1039/COLC00419G.
Sharma, V. et al. (2007) "Surface Characterization of Plasma-Treated and PEG-Grafted PDMS for Micro Fluidic Applications," Vacuum 81:1094-1100.
Shin, Y.S. et al. (2010) "Chemistries for Patterning Robust DNA MicroBarcodes Enable Multiplex Assays of Cytoplasm Proteins from Single Cancer Cells," ChemPhysChem 11:3063-3069.
Simplexa™ Flu A/B & RSV Direct Kit; Focus Diagnostics, Inc.: https://www.focusdx.com/product/MOL2650. Last Accessed May 5, 2014.
Taylor, M.T. et al. (2001) "Lysing Bacterial Spores by Sonication through a Flexible Interface in a Microfluidic System," Analytical Chemistry 73(3):492-496.
The FilmArray System; Biofire Diagnostics, Inc.: http://filmarray.com/the-panels/. Last Accessed May 5, 2014.
Wang, J, et al. (2010) "A Self-Powered, One-Step Chip for Rapid, Quantitative and Multiplexed Detection of Proteins from Pinpricks of Whole Blood," Lab Chip 10:3157-3162.
Wang, J. (2002) "Portable Electrochemical Systems," Trends in Analytical Chemistry 21(4):226-232.
Wang, J. et al. (2005) "Self-Actuated, Thermo-Responsive Hydrogel Valves for Lab on a Chip," Biomedical Microdevices 7(4):313-322.
Wu, C. et al. (2011) "Ultrasonication on a Microfluidic Chip to Lyse Single and Multiple *Pseudo-Nitzschia* for Marine Biotoxin Analysis," Biotechnology Journal 6:150-155.
Xpert® Flu; Cepheid: http://www.cepheid.com/us/cepheid-solutions/clinical-ivd-tests/critical-infectious-diseases/xpert-flu. Last Accessed May 5, 2014.
Ziegler, J. et al. (2008) "High-Performance Immunoassays Based on Through-Stencil Patterned Antibodies and Capillary Systems," Analytical Chemistry 80(5)1763-1769.
Office Action for Design U.S. Appl. No. 29/490,660, mailed Jun. 25, 2014, 6 pages.
U.S. Appl. No. 14/599,365, filed Jan. 16, 2015, Cue Inc.
U.S. Appl. No. 14/599,369, filed Jan. 16, 2015, Cue Inc.
U.S. Appl. No. 14/599,372, filed Jan. 16, 2015, Cue Inc.
U.S. Appl. No. 14/599,375, filed Jan. 16, 2015, Cue Inc.
Non-Final Office Action in U.S. Appl. No. 14/479,149, mailed Jan. 13, 2015, 17 pages.
Non-Final Office Action in U.S. Appl. No. 14/543,842, mailed Feb. 12, 2015, 11 pages.

(56) References Cited

OTHER PUBLICATIONS

Notice of Allowance in U.S. Appl. No. 14/479,149, mailed Mar. 6, 2015, 13 pages.
Non-Final Office Action in U.S. Appl. No. 14/599,372, mailed Mar. 27, 2015, 11 pages.
Restriction Requirement in Design U.S. Appl. No. 29/460,660, mailed Jun. 2, 2015, 8 pages.
Restriction Requirement in U.S. Appl. No. 14/599,369, mailed May 7, 2015, 6 pages.
Non-Final Office Action in U.S. Appl. No. 14/599,375, mailed Jun. 19, 2015, 15 pages.
Cecchet, F. et al. (2006) "Redox Mediation at 11-Mercaptoundecanoic Acid Self-Assembled Monolayers on Gold," J. Phys. Chem. B 110:2241-2248.
Yoshioka, K. et al. (2010) "Suppression of Non-specific Adsorption Using Densified Tri(ethylene glycol) Alkanethiols: Monolayer Characteristics Evaluated by Electrochemical Measurements," Analytical Sciences 26:33-37.
Notice of Allowance in U.S. Appl. No. 14/543,842, mailed Apr. 24, 2015, 8 pages.
Notice of Allowance in U.S. Appl. No. 14/599,365, mailed May 1, 2015, 8 pages.
Non-Final Office Action dated Aug. 18, 2015 in U.S. Appl. No. 14/599,369.
U.S. Notice of Allowance dated Aug. 20, 2015 in Design U.S. Appl. No. 29/490,660.
U.S. Notice of Allowance dated Aug. 26, 2015 in U.S. Appl. No. 14/599,375.
U.S. Notice of Allowance dated Sep. 14, 2015 in U.S. Appl. No. 14/599,372.
Lomas, N. (2014) "Cue Is a Connected Lab-In-A-Box for On-Demand Health Testing At Home," TechCrunch.
Prindle, D. (2014) "Sick? Need more vitamin D? Testosterone? Lick a stick and Cue fills you in," www.digitaltrends.com.
International Search Report and Written Opinion (ISA/EP) for International Application No. PCT/US2015/049439, dated Dec. 7, 2015, 15 pages.
Final Office Action in U.S. Appl. No. 14/599,369, dated Jan. 4, 2016.
Non-Final Office Action in U.S. Appl. No. 14/954,817, dated Feb. 2, 2016.
Supplementary Partial European Search Report in European Application No. 14779852.4, dated Feb. 11, 2016.
U.S. Appl. No. 29/574,538, filed Aug. 16, 2016, Cue Inc.
Notice of Allowance in U.S. Appl. No. 14/954,817, filed Nov. 3, 2016.
U.S. Appl. No. 29/545,014, filed Nov. 9, 2015, Cue Inc.
Corrected Notice of Allowability in U.S. Appl. No. 14/599,369, dated May 11, 2016.
Final Office Action in U.S. Appl. No. 14/954,817, dated May 23, 2016.
Restriction Requirement in Design U.S. Appl. No. 29/545,014, dated May 10, 2016.
Extended European Search Report in European Application No. 14779852.4, dated Jul. 20, 2016.
Advisory Action in U.S. Appl. No. 14/954,817, dated Sep. 19, 2016.
Notice of Allowance in U.S. Appl. No. 29/545,014, dated Sep. 2, 2016.
International Search Report and Written Opinion, PCT/US2016/042688, Cue Inc, 16 pages (dated Jan. 10, 2017).
Notice of Allowance in U.S. Appl. No. 15/336,735, dated Jan. 5, 2017.
Notice of Allowance on U.S. Appl. No. 29/574,538 dated Feb. 17, 2017.
U.S. Non-Final Office Action dated Feb. 9, 2017 in U.S. Appl. No. 15/336,715.
U.S. Non-Final Office Action dated Jan. 27, 2017 in U.S. Appl. No. 15/336,502.
U.S. Non-Final Office Action dated Jan. 30, 2017 in U.S. Appl. No. 15/336,487.
U.S. Non-Final Office Action dated Mar. 16, 2017 in U.S. Appl. No. 15/336,712.
U.S. Non-Final Office Action dated Mar. 21, 2017 in U.S. Appl. No. 15/336,739.
U.S. Notice of Allowability in U.S. Appl. No. 15/336,735, dated Feb. 13, 2017.
U.S. Notice of Allowance in U.S. Appl. No. 15/172,077, dated Feb. 10, 2017.
U.S. Supplemental Notice of Allowability in U.S. Appl. No. 15/172,077 dated, Mar. 7, 2017.
Notice of Allowance in U.S. Appl. No. 14/599,369, dated Apr. 22, 2016.
U.S. Notice of Allowance in U.S. Appl. No. 15/336,487, dated Jun. 6, 2017, 26 pages.
U.S. Notice of Allowance in U.S. Appl. No. 15/336,715, dated May 17, 2017, 17 pages.
International Preliminary Report on Patentability, PCT/US2015/049439, Cue Inc., 10 pages (dated Mar. 23, 2017).

\* cited by examiner

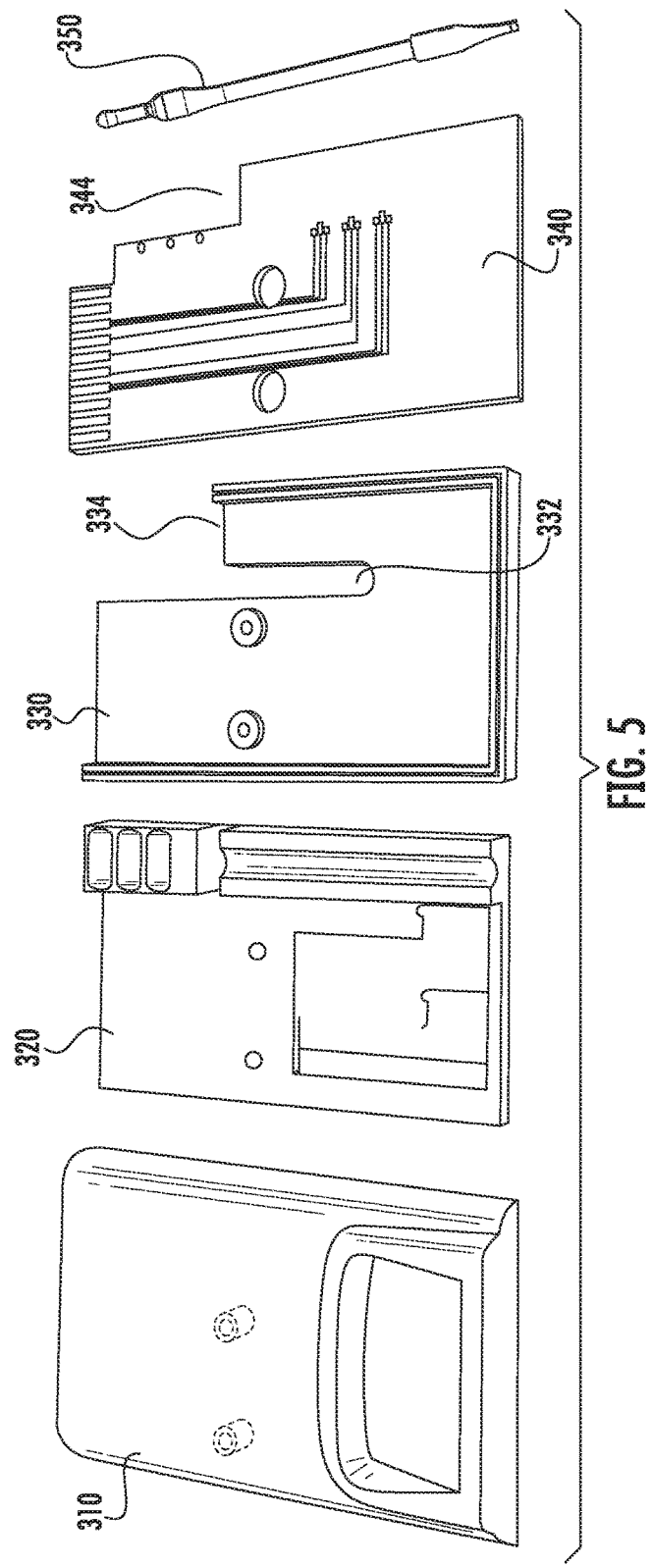

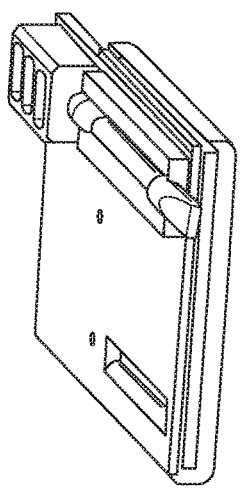
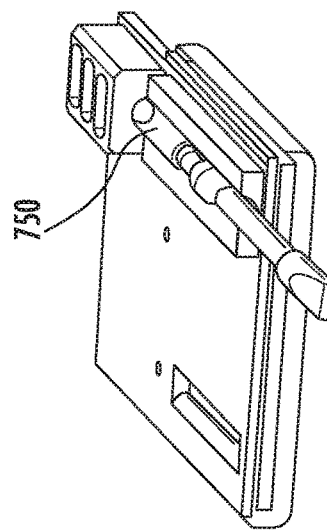
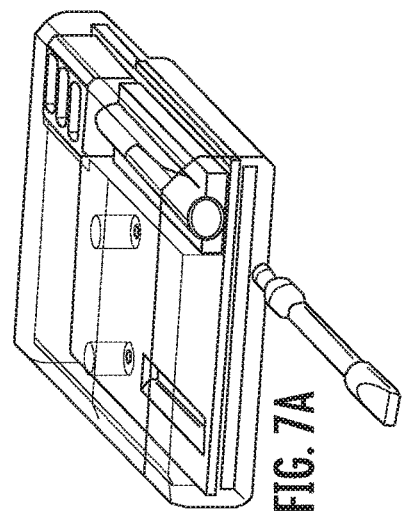

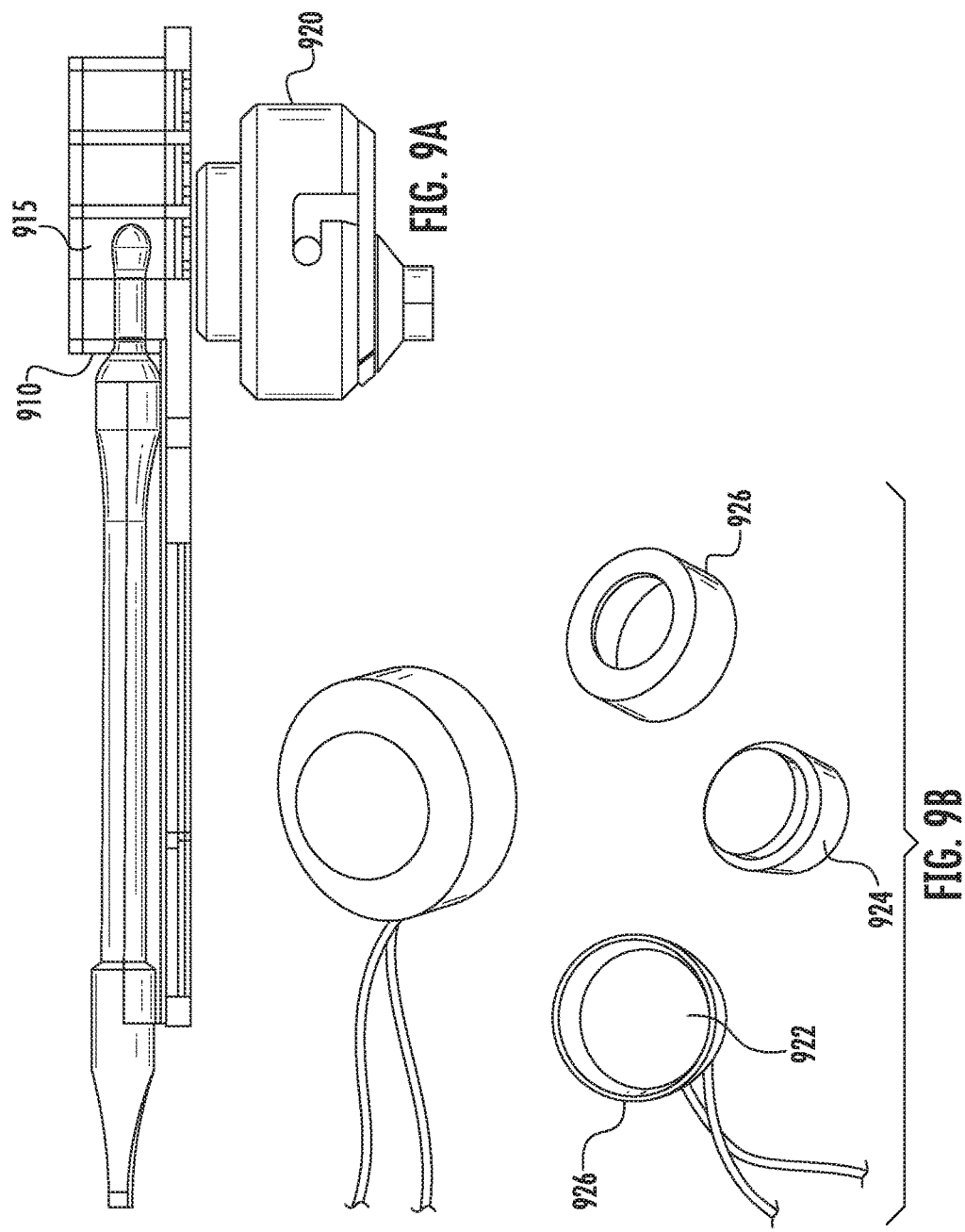

(i) t = 2s after swab entry     (ii) t = 10s after swab entry

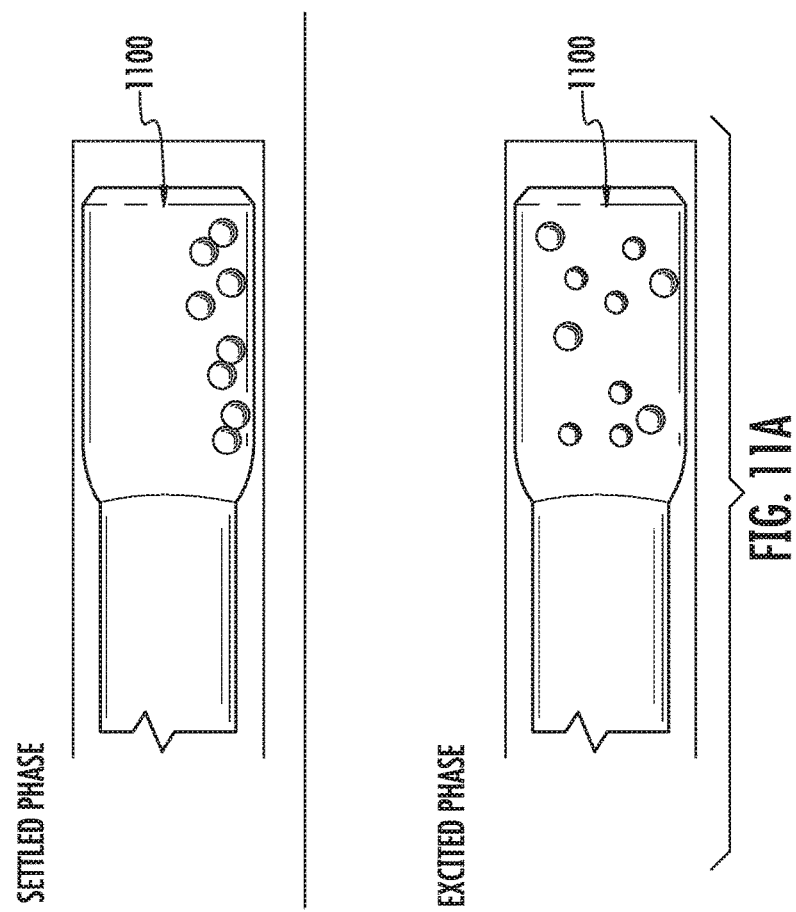
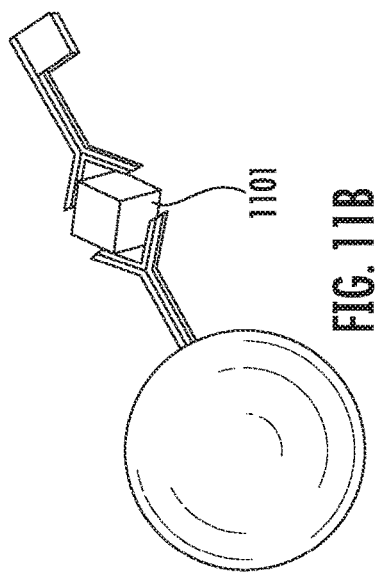
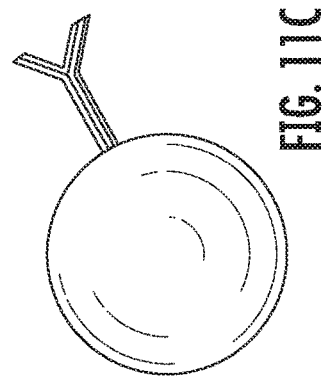

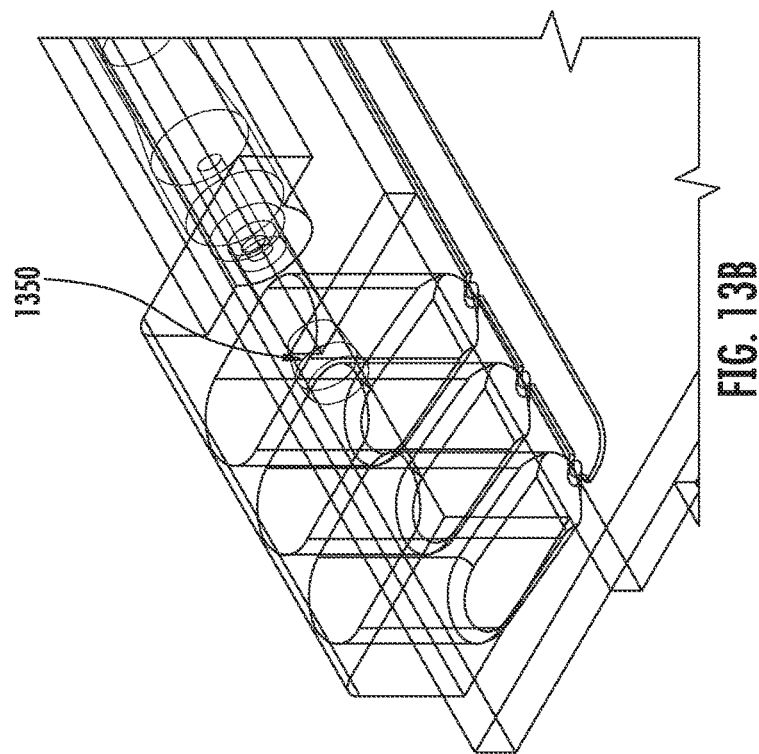
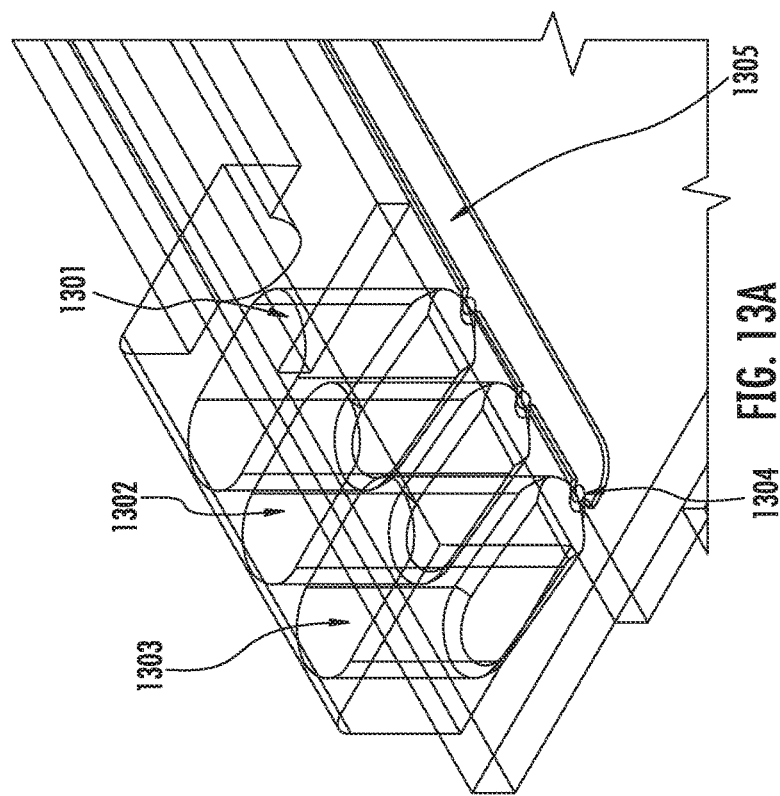

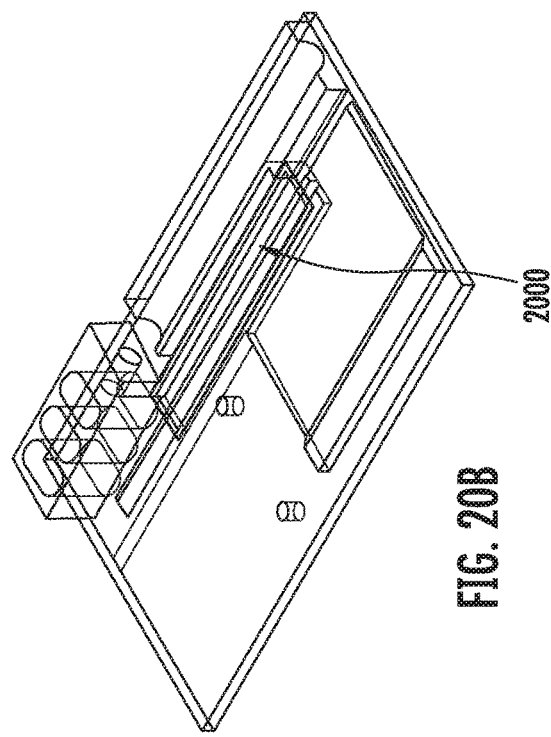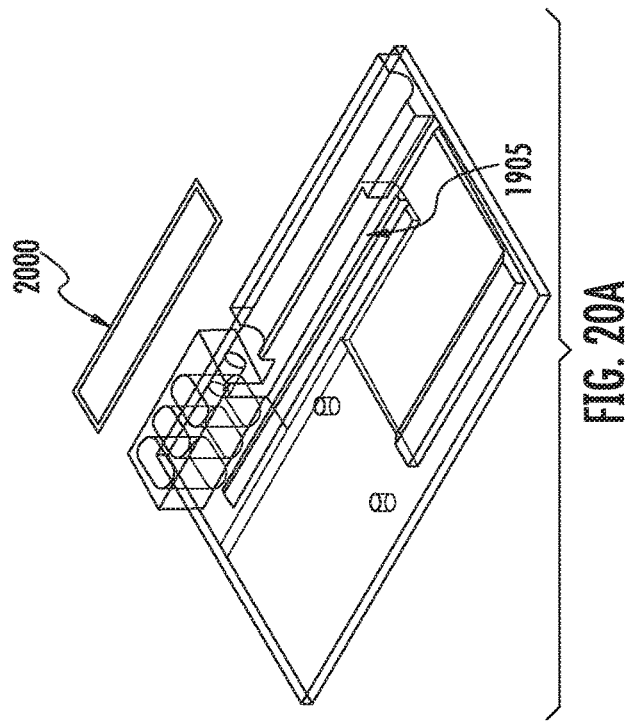

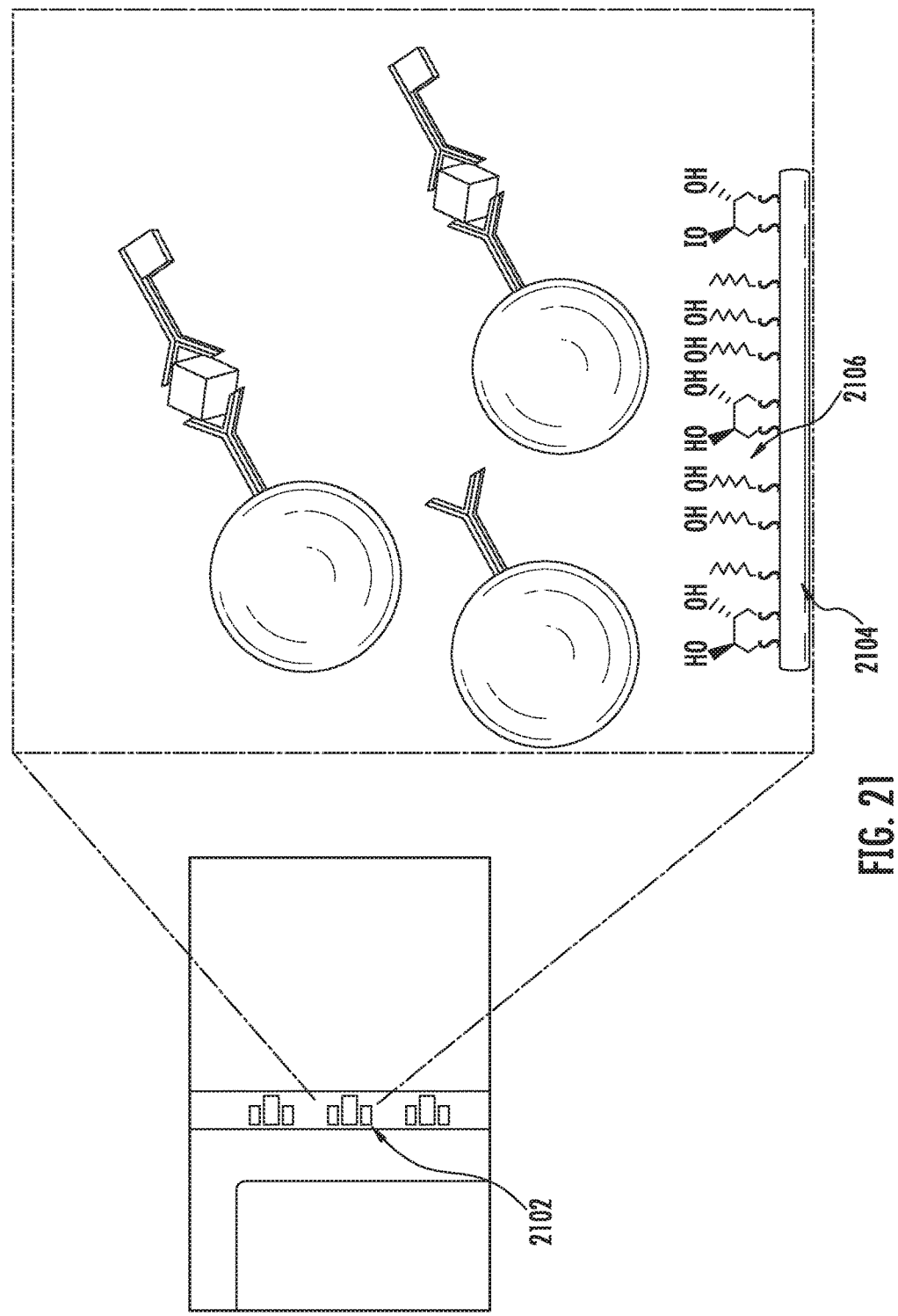

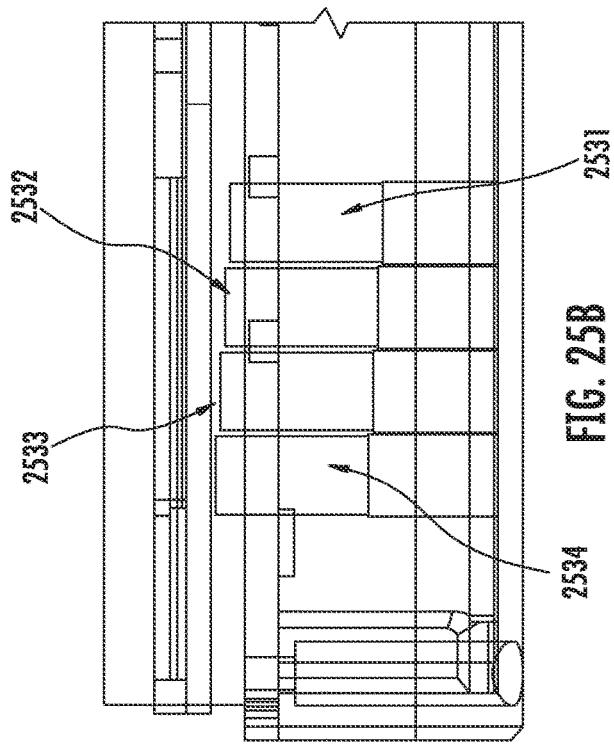
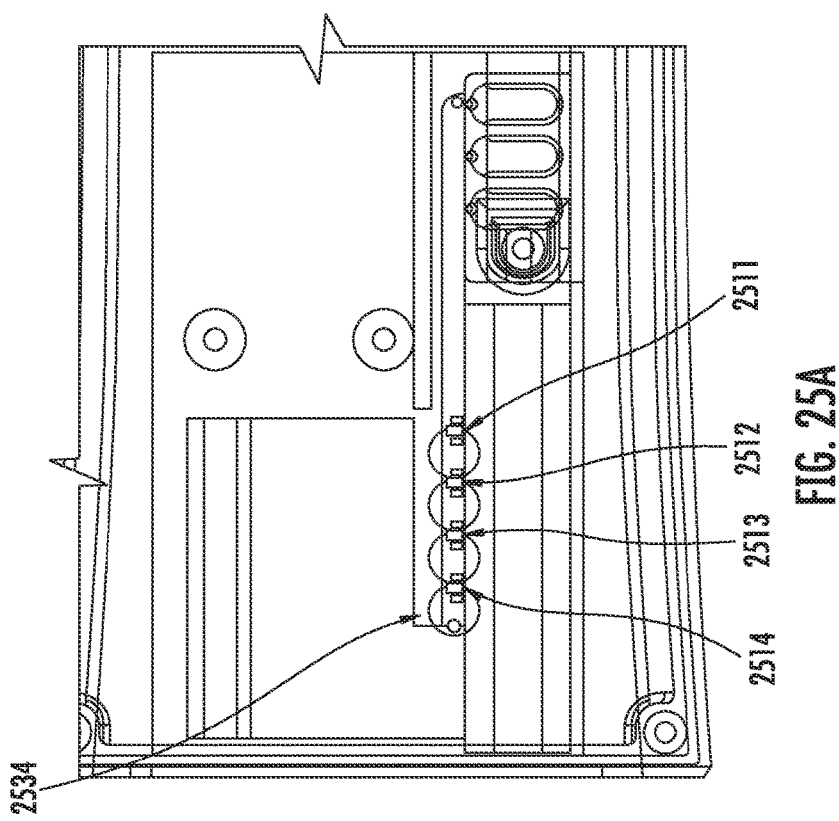

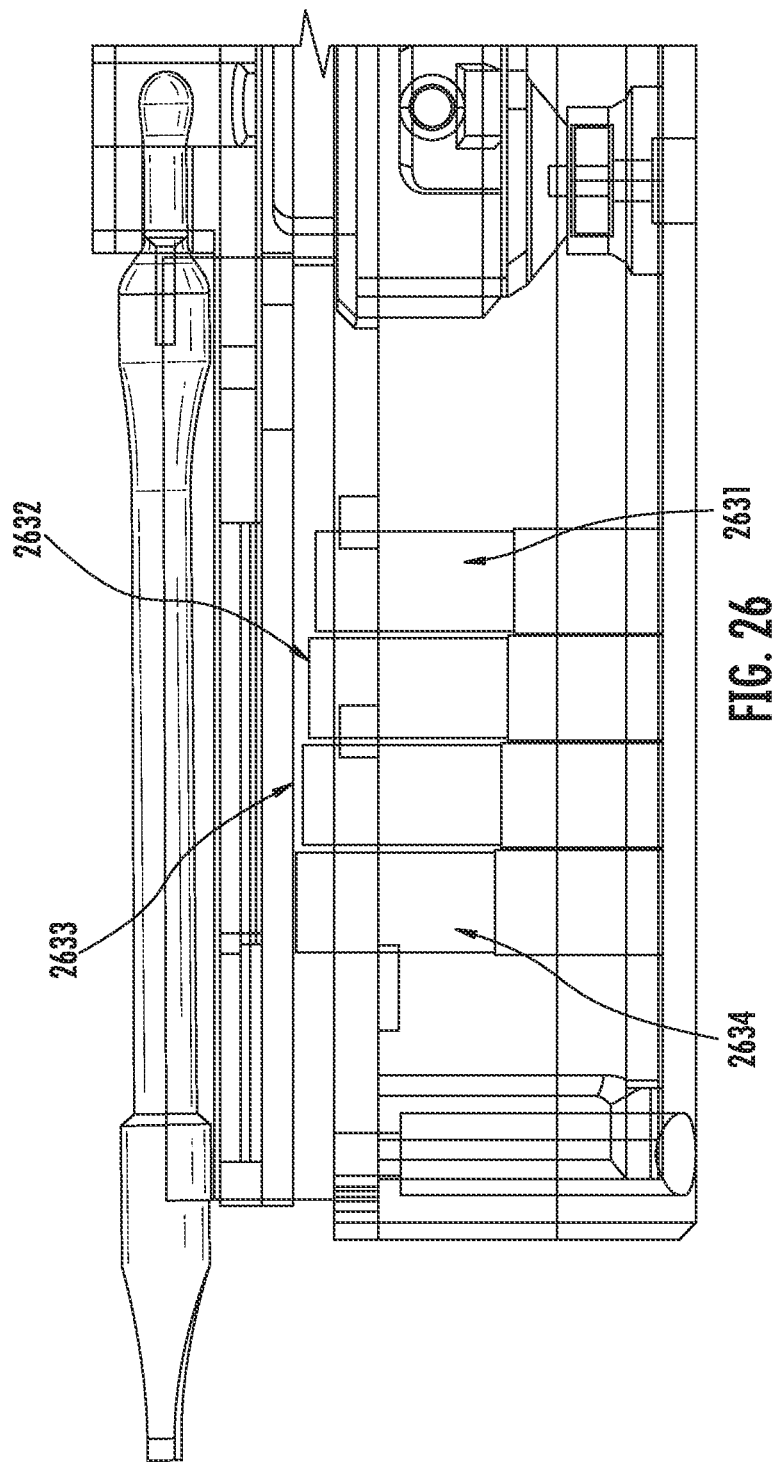

SYSTEM FOR PORTABLE AND EASY-TO-USE DETECTION OF ANALYTES WITH MOBILE COMPUTING DEVICE

CROSS-REFERENCE TO RELATED PATENT APPLICATIONS

This application claims the benefit of and priority to U.S. Provisional Application No. 61/776,254, filed Mar. 11, 2013, entitled SYSTEM FOR PORTABLE AND EASY-TO-USE DETECTION OF ANALYTES WITH MOBILE COMPUTING DEVICE, which is hereby incorporated by reference in its entirety.

FIELD OF THE INVENTION

The present disclosure relates generally to technologies for identifying the presence, absence and/or quantity of nucleic acids, proteins, and/or other molecules of interest within a sample.

BACKGROUND

Conventional technologies for identifying the presence, absence and/or quantity of nucleic acids, proteins, and/or other molecules of interest within a sample often require expensive laboratory equipment and the expertise of highly-trained medical professionals. Consequently, such analyses are typically performed within laboratories or medical facilities. Such molecule detection can be important, for example, to detect the presence of pathogens, disease, contamination, overdoses, and poisonings within an individual or other animal or the environment. Unfortunately, today, individuals may face long waits before the proper tests can be performed and the results can be generated and analyzed.

SUMMARY

There is a significant need for improved molecule detection technologies. Various embodiments disclosed herein may such a need.

The disclosed system takes in raw cellular material collected using a provided swab, blood collection device, urine collection device, or other sample collection device and transforms that biological material into a digital result, identifying the presence, absence and/or quantity of nucleic acids, proteins, and/or other molecules of interest. The system has several innovative components and subsystems to achieve the result.

Overall, the architecture of the system includes a reader component, a cartridge component that fits into the reader, a sample collection component that fits into the cartridge in the reader, and also a mobile computing device, such as but not limited to a smartphone or tablet PC such as an iPad®. Preferably, the reader communicates with the external mobile computing device through wireless communication, especially Bluetooth® protocols.

The mobile computing unit uses an App, or software application, to send and receive signals with the reader, including new testing protocols, tests results, and more. The ability to add testing protocols has significant advantages for the system because this allows for same onboard reader hardware to execute tests with new cartridges released after the reader is already produced and in the hands of the user.

The mobile communication device allows for communication of the result to physicians, recording of the result, and other options as described herein.

BRIEF DESCRIPTION OF THE DRAWINGS

Exemplary embodiments are described below with reference to the accompanying drawings. In the drawings:

FIG. 5 depicts an overview of the cartridge.

FIG. 7A-C depict an embodiment of the sample input mechanism.

FIG. 9A-B depict various views of a sonicator.

FIG. 11A-C schematically represents the physical and chemical changes that result from sonication.

FIG. 13A-B depicts one embodiment of the reservoirs of the cartridge, without and with a swab, respectively.

FIG. 20A-B depicts perspective views of one embodiment of the microfluidic channel and reservoir component, before and after a membrane is placed and bonded on the component.

FIG. 21 depicts one embodiment of sensors with microbeads localized over it; a schematic representation of such microbeads is also provided.

FIG. 25A-B depicts a top view and a side view, respectively, of one embodiment of a cartridge designed for multiplexing.

FIG. 26 depicts a side view of another embodiment of a cartridge designed for multiplexing.

DETAILED DESCRIPTION OF CERTAIN EMBODIMENTS

The system disclosed herein takes in raw cellular material collected using a provided swab, blood collection device, urine collection device, or other sample collection device and transforms that biological material into a digital result, identifying the presence, absence and/or quantity of nucleic acids, proteins, and/or other molecules of interest. The system has several innovative components and subsystems to achieve the result.

Overall, the architecture of the system includes a reader component, a cartridge component that fits into the reader, a sample collection component that fits into the cartridge in the reader, and also a mobile computing device, such as but not limited to a smartphone or tablet PC such as an iPad. The overall architecture is shown in FIGS. 1-4. Preferably, the reader communicates with the external mobile computing device through wireless communication, especially bluetooth protocols. As shown specifically in FIG. 1, the system 100 consists of a durable universal reader and a disposable cartridge and swab. Communication between a smartphone and reader occurs through Bluetooth 4.0 (Bluetooth Low Energy), for example. Operating the device at a high level involves the following: 1) the user loads the cartridge into the reader, 2) swabs his nose and inputs it into the cartridge, 3) the test is run from a mobile app (iPhone), and the results are displayed in the app as well.

The mobile computing unit uses an App, or software application, to send and receive signals with the reader, including new testing protocols, tests results, and more. The ability to add testing protocols has significant advantages for the system because this allows for same onboard reader hardware to execute tests with new cartridges released after the reader is already produced and in the hands of the user.

The mobile communication device allows for communication of the result to physicians, recording of the result, and other options as described herein.

Cartridge Loading

Figure 1:
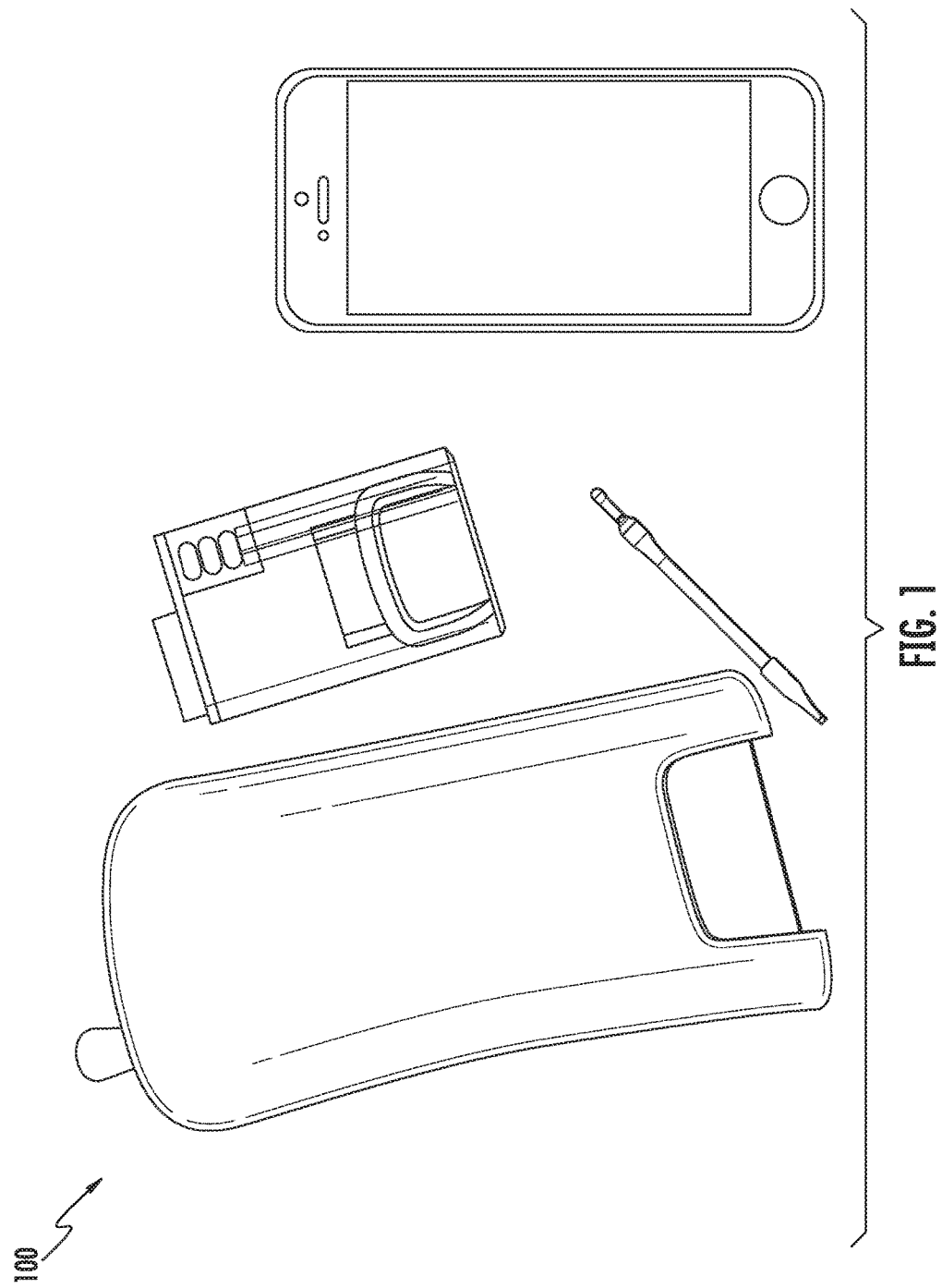
FIG. 1 depicts one embodiment of a system for detecting analytes.
Figure 2:
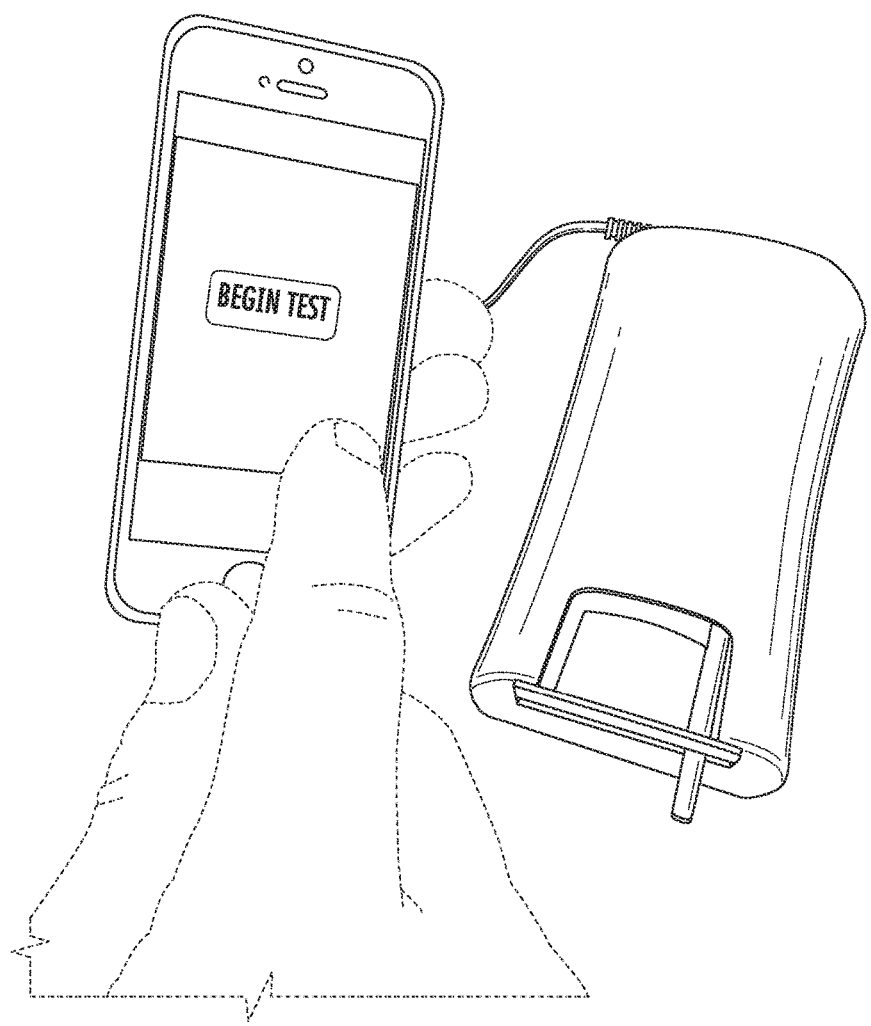
FIG. 2 depicts another embodiment of the system.
Figure 3:
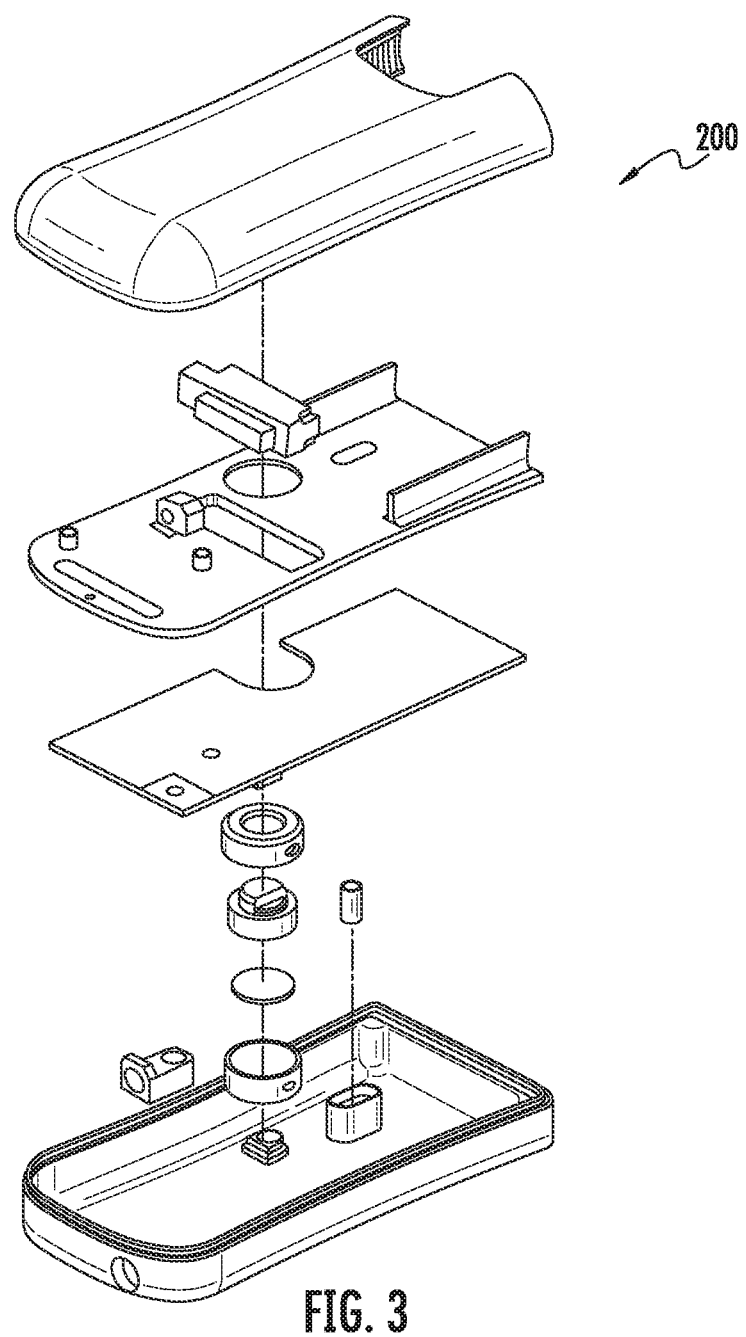
FIG. 3 depicts an exploded view of one embodiment of a reader.
Figure 4:
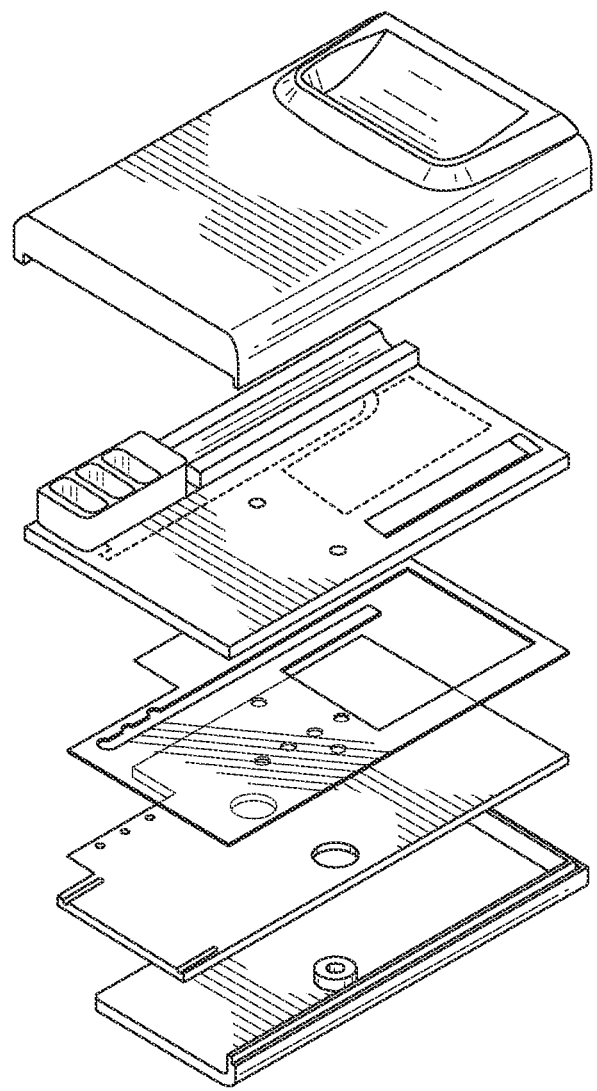
FIG. 4 depicts an exploded view of one embodiment of a cartridge. Note that the actual component breakdown of the cartridge is on FIG. 5. This figure should not be used as a reference for component parts, but rather as an example of how the cartridge stacks together into one unit.

The system is operated by first loading the cartridge into the reader 200 as in FIG. 3. The cartridge 300, as shown in FIG. 5, includes: a cover 310, which contains part of a swab input tunnel; a microfluidic component 320, which includes reservoirs, part of the swab input tunnel, an internal membrane for swab input, area for an absorbent pad, a microfluidic channel, and holes for wax valves over vias; a base 330 with a magnet cutout/slot 332 for sliding a permanent magnet into place during cartridge loading; the base 300 also has a cutout 334 for sonicator access to the reservoir; a PCB 340 with sensors and valves and sonicator slot 344; and a swab 350 where the top is the head for sample collection and input, and the swab has a neck for sealing. The cartridge contains a slot to allow for the permanent magnet or magnets to slide into place underneath the sensor component (labeled 332 in FIG. 5). This allows for the magnet to be as close to the sensor as possible, allowing for a greater magnetic field to be exerted, which is preferable to be able to utilize smaller magnets in bead capture (as described in another section) with less overlapping fields or "crosstalk" of magnetic fields.

The cartridge establishes electrical connections with the reader. In one embodiment, this can be done with the leads shown at the top of the sensor component plugging into what is known as an "EDGE card", a connector with pins to establish electrical continuity. These connections establish electrical continuity between the electrodes on the sensor component and the electrochemical circuitry on the reader. Additionally, the resistive heaters on the sensor component establish electrical continuity with the circuitry to establish current flow through the resistive heaters for valve actuation as described in the valve section. Other connector schemes can be employed to achieve electrical connections between the sensor component of the cartridge and the reader.

The sensor component and the base of the cartridge also have a cutout to permit access of the sonicator piece to the reservoirs, particularly the sample preparation/input reservoir (see FIG. 5). When the user slide the cartridge in, the cutout allows for the sonicator to be positioned directly underneath the reservoir. With the cutouts in the sensor component and base component of the cartridge, the sonicator component can directly access reservoir 1 on the microfluidics component.

Underneath the reservoir, a high water content blister can optionally be affixed in the cartridge production process such that the sonic energy conducted from the piezo component can be delivered with minimal attenuation into the reservoir during testing. This blister, or other appropriately conducting sonication medium, is preferably dry on the outside, with no liquid residue left behind. When the cartridge slides into the reader, the sonically conducting medium affixed to the piezo disc forms a soft seal with the sonically conducting medium affixed to the bottom of the reservoir. This "soft seal" is enhanced by using a conformal sonically conducting medium on the bottom of the reservoir.

Additionally, the side of the reader can optionally have a pressure sensitive piezo electric component for sensing flex in the sample input reservoir. This allows for a pressure sensitive start to the test as soon as a sample input device has entered into the reservoir.

To turn on the reader and to prompt a connection to the user's smartphone, the piezo cartridge has been inserted. Alternatively, the electrical connections between the cartridge and reader can perform the function to turn on the reader, alert the reader to the presence of an inserted cartridge, and/or search for and connect to nearby smartphones that could be the users.

This particular function described in the preceding paragraph can be actuated by simply allowing a circuit to be completed with the addition of the cartridge based on electrical continuity between the reader and the cartridge, just the same as a switch turns on an electrical circuit.

A resistor can be added to the sensor component that allows for the reader to distinguish between cartridges. In other words, if a cartridge is added with a small surface mount resistor, or a resistive-ink based resistive element, the reader can "read the resistor" using circuitry on the reader. If the cartridge is recognized, the reader will prompt to open an App established for this particular cartridge and/or a protocol on the App designated for this cartridge. If the resistor is not recognized as a currently available cartridge, then the user will be prompted to either update the App designated to run the test, or download the proper App for running the test.

A default App can have a stored list of values for different possible resistor values that helps facilitate locating the proper App to run the test.

Once the proper App is located, the proper testing protocol will be added to the reader's list of supported tests associated to the particular resistance value of the cartridge. In other words, the new testing protocol is loaded through wireless communication (i.e. bluetooth) onto the reader so that future tests with this cartridge will automatically be recognized and performed without the need for searching for a new protocol.

Figures 6A, 6B:
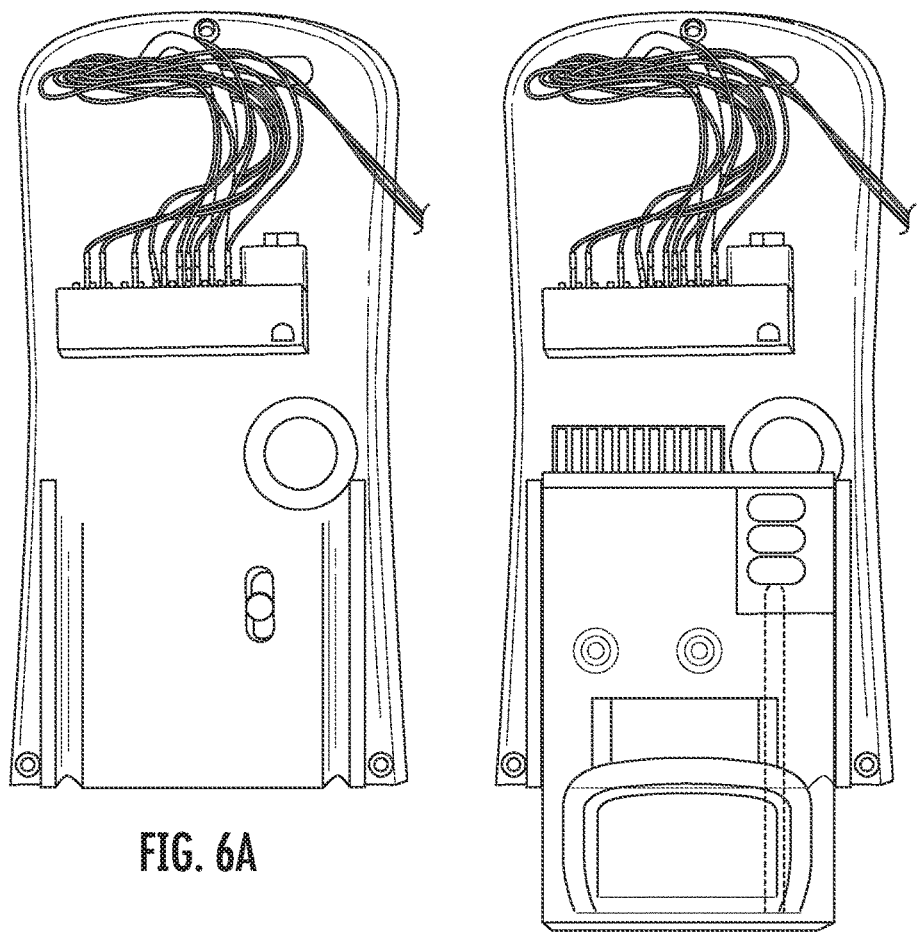
FIG. 6A-B depict an example of cartridge loading into the reader.
Figure 8A:
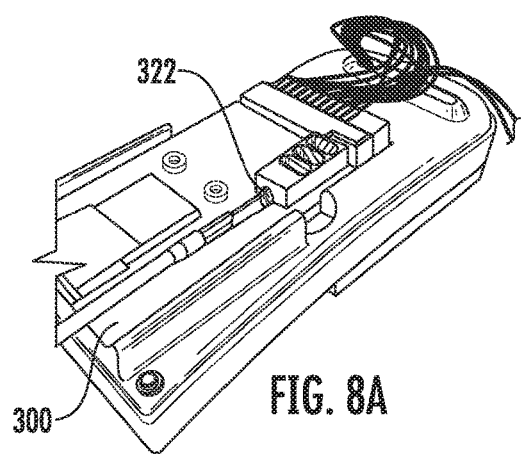
FIG. 8A-D depicts one embodiment of inserting a swab into the cartridge.
Figure 8B:
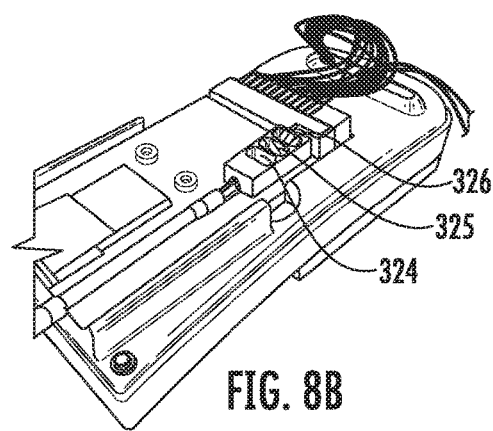
Figure 8C:
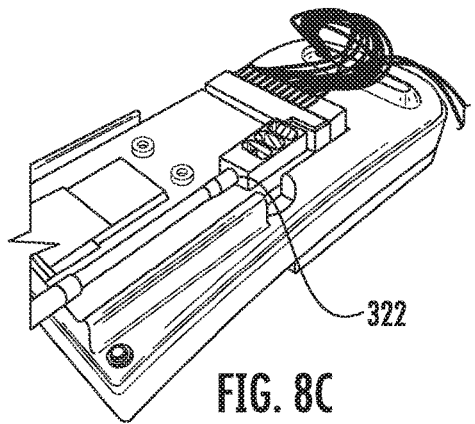
Figure 8D:
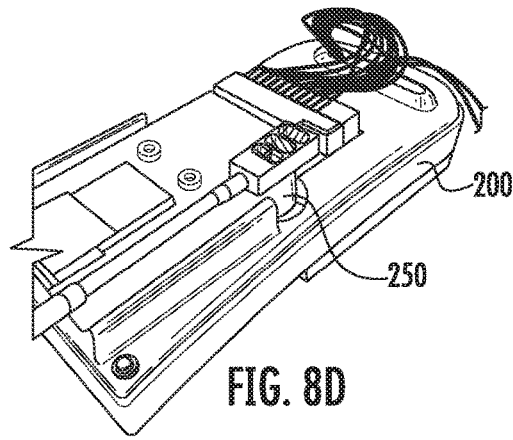

An example of cartridge loading is provided in FIGS. 6A-6B. In FIG. 6A, we are looking at the reader from above. The top is removed for the view. As shown in FIG. 6B, the user loads the cartridge into the reader. The cartridge establishes electrical connections with the reader via an edge card connector. The permanent magnet slides into place beneath the sensors for magnetic bead capture. This sliding into place happens without bumping into the cartridge—made possible by the cutout in the base of the cartridge, and also allows for close proximity of the magnet to the microfluidic channel to attract beads onto the sensor. The cutout in the base and the sensor component allows for a piezo to slide into place underneath the reservoir for sample preparation.

Leakage-Free Rupture of Internal Membrane

This sections figures are FIGS. 7-9. The user pushes the swab into the plastic cartridge and the swab locks into place automatically. The swab head ruptures an internal membrane containing a volume of liquid. The liquid allows for material collected on the swab to be suspended in the fluid for analysis, as described in follow sections.

In FIGS. 7A-C, a sample input mechanism is shown. In FIG. 7A, the cartridge contains a swab input tunnel. At the end of the tunnel, we have a membrane covering the entry port to the first reservoir. This is what we call the internal membrane. FIG. 7B shows the swab traveling through the swab tunnel (the cover is made invisible here) towards the area for the internal membrane 750. FIG. 7C shows the swab piercing the membrane and entering the first reservoir.

In the example of FIG. 8, the cartridge 300 includes a membrane 322, a first reservoir 324, a second reservoir 325, and a third reservoir 326. The reader 200 includes a sonicator 250. In FIG. 8, at FIG. 8A, when the user inserts the swab into the cartridge 300, the swab head pushes the membrane 322 in, as shown at FIG. 8B. It then ruptures the membrane 322, right as the neck of the swab takes up position where the membrane 322 was located to seal off the reservoir 324 and prevent leakage, as shown at FIG. 8C-8D. The swab head is located in reservoir 324, directly over the sonicator 250, as depicted. Inside this reservoir 324, we have a volume of liquid that contains several components as discussed elsewhere herein. (Note that the cover for the microfluidics, which makes up the top of the swab input tunnel, is not shown in FIG. 8).

The swab head is meant to rupture an internal membrane, yet there are two reasons the swab head is blunt:
(a) the user should not be able to hurt themselves with a sharp swab head
(b) in our approach to rupturing the internal membrane, it is critical that the swab is blunt enough that it doesn't immediately pierce the membrane. Instead, it continuously deforms the membrane to the rupture point.

Two critical events happen at the instant the swab pushes the membrane to its rupture point:
a) The rubber gasket at the base of the swab head has moved into position to form a seal with the structural material surrounding the membrane.
b) The swab shaft is far enough inside the plastic cartridge's tunnel that the swab locks into place. The locking into place is critical to maintain some structural support for preventing leakage. In particular, the swab being locked into place allows the swab seal to resist the pressure exerted on the head during rupture of the membrane.

Every material has a modulus of elasticity, which is a constant that allows a calculation of when a material retains its elasticity, i.e. how much the membrane can be stretched yet will return to its original shape. This point is called the yield point. Beyond the yield point, the material exhibits plasticity rather than elasticity, where it deforms and no longer returns to its original shape. Beyond the yield point is another critical point called the rupture point. The rupture point is when the membrane breaks. If instead the swab head was sharp or the membrane material had a very small rupture point, the swab would quickly pierce the membrane, making it very difficult to contain the liquid as it spilled from the membrane. A blunt swab with an appropriate deformable membrane allows the swab's gasket to get into place to prevent leakage is key. Elastic membrane materials are readily obtained from polyurethane, polysilicone and polybutadiene, and nitrile for example. Deformable, inelastic diaphragms are made with polyethylene terephthalate (PET), mylar, polypropylene, polycarbonate, or nylon, for example. Other suitable materials for the deformable film include parafillm, latex, foil, and polyethylene terephthalate. Key factors in selecting a deformable film include the yield point, rupture point, and elastic modulus.

The size of the swab head and the rupture point of the membrane material and the location of the internal grooves must be decided in consideration of each other.

Swab Locking and Clicking into Place

The swab clicks or locks into place because of matching positive and negative grooves in the tunnel. The positive grooves are radially placed in the tunnel and negative grooves are placed on the shaft of the swab. They are formed such that when the swab shaft moves past them they are compressed slightly, but as soon as the swab is in the right location, they lock into the matching groove on the swab. The reason for this structure is three fold:
(a) there should be tactile confirmation for the user that the swab was inserted correctly to help them ascertain the proper depth of swab input
(b) the two-way lock gives structural support to the rupture/seal mechanism
(c) the two-way lock prevents the user from taking the swab out of the cartridge
(d) radial placement allows for non-oriented insertion of swab by the user; the negative groove on the swab can be just a single groove along the circumference of the shaft.

By two-way lock, we mean that the positive and negative grooves are deep enough that they prevent the user from both 1) being able to push the swab in further and 2) pull it out. Preventing the user from taking out the swab is important because this allows for the easy disposability of the system into normal trash and also prevents the user from coming into contact with contaminated items. This is a significant advantage from a biohazard trash perspective.

Pressure Sensitive Auto-Start to Test

Once the cartridge is loaded into the reader, we need a 1-step method for starting the test. In other words, we would like for the user to be able to input the sample input device, such as the swab, blood lance, saliva collector and have the test start upon inserting this input device into the cartridge without having the user required to push a button. This can be accomplished with the following method.

The reservoir accepting the input is made to flex slightly such that upon the input devices entry into the reservoir, the flex outward occurs. A pressure sensitive sensor on the reader, such as a piezo electric sensor, in contact with the reservoir then reports the pressure change to the processing unit on the reader, which in turn begins the testing protocol.

For example, as shown in FIG. 9A, the swab insertion, which moved the swab passed the membrane area 910 into the first reservoir 915, has brought the head containing the sample directly over the sonicator 920. The sonicator 920 directs all of its energy into this first reservoir 915 to mix the sample on the swab head with the reagents. As shown in FIG. 9B, the sonicator piece consists of a piezo disk 922, a piece of material called Aqualene 924 that conducts high frequency sound waves and a cup 926 for holding the parts together. Other sonically conducting mediums can be appropriate. Additionally, on the underside of the reservoir, a sonically conducting medium can be affixed such that a soft seal is formed between the conducting medium permanently affixed to the piezo component and the reservoir.

The pressure sensitive piezo and the flex region of the cartridge can be anywhere along the swab input tunnel, as long as the change in pressure occurs as the swab head actually inserts into the input.

Upon receiving the increased pressure and upon conversion into a signal the microcontroller on board can read as a test initiated signal, the microcontroller will start the testing protocol and send notification via wireless communication to the mobile computing unit (i.e. iPhone®) and suggest to open the App, while maintaining a timer than can be used to update the iPhones progress bar for test completion percentages and estimated time to completion.

The key points are for the reservoir, or other area along the input tunnel to flex outward increasing the pressure on a pressure sensor on the reader in contact, which will then initiate the testing protocol and possibly inform the remote, mobile computing device (smartphone, tablet, etc.).

Other Sample Collection Devices

Swabs are not the only sample input device that can be used to input sample into the cartridge. Alternative collection devices, such as one that wicks a small droplet of blood or urine into a small capillary channel can be used to input collected sample into the reservoir as well. Throughout this document, swab head will be the term used to reflect the sample collection portion of any sample input device.

Sample Preparation

Figure 12:
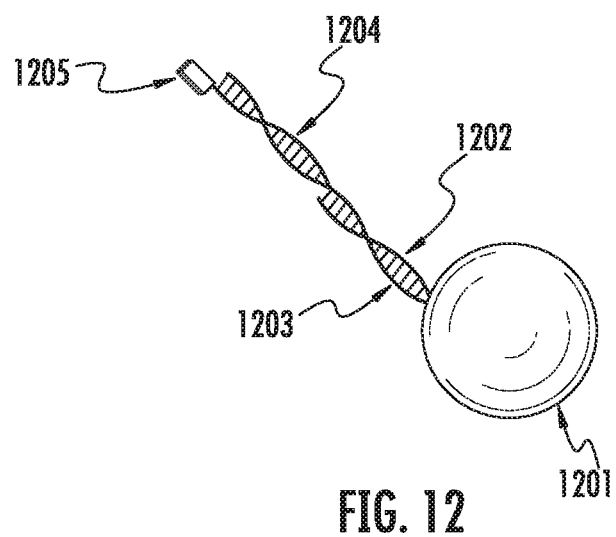
FIG. 12 schematically represents a nucleic acid sandwich complex.

This sections figures are FIGS. 9-14. At the input reservoir (where the swab head enters), a liquid volume is present to recover sample on the swab head. This material, be it nasal sample, blood sample, etc. potentially has an analyte of interest to be tested. Therefore, in this input reservoir, there are several important components to accomplish the key objective of the sample preparation phase: to assemble a sandwich complex onto one or more populations of microbeads or nanoparticles using antibody probes or nucleic acid probes or other affinity reagent as depicted in FIGS. 10b and 12.

The components in the liquid reservoir needed to form the sandwich complex include the (a) components that actually make up a bead-based sandwich complex: microbeads/nanoparticles with surface bound affinity molecules (antibodies, nucleic acid probes, etc.), detector agents such as antibodies conjugated to signaling enzymes, labeled nucleic acid probes to which signaling enzyme can bind; (b) agents that facilitate formation of the sandwich complex such as salts; (c) agents that facilitate access and specificity to target analytes such as detergents and enzymes for lysis or chopping up larger nucleotides into smaller pieces; (d) blocker proteins to decrease nonspecific binding of signaling enzyme or targets onto microbeads and sensors downstream; (e) stabilizers such as trehalose that can keep the components in the reservoir functional throughout a long shelf life.

Components that make up a bead-based sandwich complex include: Microbeads/nanoparticles, and there can be multiple populations of these, each with their own affinity (in other words a different antibody or set of antibodies or dna probes per population of bead), signaling enzyme, "detector" antibody or another antibody or nucleic acid that has affinity to another portion of the analyte of interest and a signaling enzyme, such as horseradish peroxidase or soybean peroxidase. The sandwich complex is well known in ELISA and there are multiple possible combinations to form such a complex. A common one is depicted in FIG. 11B-C for antibodies detecting proteins or small molecules of interest and FIG. 12 for nucleic acids with sequence specificity. Additionally nucleic acid aptamers could be the affinity unit on the surface of the bead or other affinity molecules. As shown in FIG. 11B, if target 1101 is present, the capture antibody will grab the target 1101 and the signaling antibody will also grab hold of the target, forming a sandwich complex. This signaling antibody's attached HRP enzyme will then cause a signal to occur at the sensor downstream. As shown in FIG. 11C, if target 1101 is not present, the signaling antibody/enzyme will not attach to the bead and will not form a complex with the bead and downstream no signal will be generated over the sensor.

The example nucleic acid sandwich complex of FIG. 12 includes: a micro bead 1201, probably magnetic; a capture probe 1202 fixed to the surface of the bead 1201, it being a DNA nucleic acid probe; a single stranded nucleic acid target 1203, either RNA or DNA—note that this piece has more bases than either the capture probe 1202 or a detector nucleic acid probe 1204 such that the capture probe 1202 can hybridize to a portion of this target 1203 and there still be bases available for hybridization for the detector nucleic acid probe 1204, which possesses the detector complex; a detector nucleic acid probe 1204 labeled on the end distant from the bead 1201 such that it can host an hrp enzyme 1205; and a signaling enzyme 1205 can be bound to a detector nucleic acid probe 1204 through common labeling scheme affinity such as: HRP conjugated to streptavidin binds to biotin-labeled detector probe 1204.

The possibilities for forming the complex are endless and include using a biotin labelled antibody which binds to a portion of the target, antibodies and nucleic acids can both be pre-biotinylated such that a streptavidin conjugated signaling enzyme such as HRP can then bind the biotinylated detector to form a complex. This confers a target specific binding of HRP onto the bead and is quantitative to the amount of the target captured. The label combination is of course not limited to biotin-streptavidin. Any suitable labeling scheme will work. Additionally, multiple HRP enzymes can be conjugated together into a molecule commonly known as a Poly HRP molecule such that the signal generating capability of a sandwich complex can be enhanced.

Salts are necessary in the input reservoir to enhance the likelihood of binding. There are some salt combinations that will interfere with electrochemical detection downstream, but phosphate buffered saline is an appropriate solution with the right salts to contain all of the components in.

Blocker proteins, such as the well-known Bovine Serum Albumin, Casein, Fibrinogen, etc. that help to stabilize other proteins such as antibodies and enzymes, but also help to prevent non-specific binding of HRP or other signaling enzymes to the beads and to the channel walls (in the microfluidic system described later) are used in the system as well.

Additionally, for assays that require lysis, detergents are often required. Nonionic detergents, rather than ionic detergents, are necessary as to not denature the signaling enzyme or antibodies in the solution. Detergents can enhance lysis of bacteria, but are also useful for gently lysing various viruses, such as the influenza virus. This is desirable to improve access to targets such as nucleoproteins that are internal to the virus.

Enzymes that enhance lysis and reduce viscosity during lysis are also a necessary component in the preparation of samples containing bacteria, for instance *E. coli*. The enzymes that facilitate lysis include lysozymes and DNAses that do not disrupt the probes on the surface of the microparticle but do chop up genomic DNA released are useful for preventing severe increases in viscosity that hamper bead movement.

Enzymes such as RNAses or DNAses that selectively chop larger nucleotide sequences into smaller sequences can be useful for generating smaller fragments that show favorable binding kinetics.

Another component is a stabilizer agent such as trehalose, which helps protect proteins from oxidation and therefore increases the shelf-life of the solution, especially at room temperature.

With the sample collection device entering the sample preparation reservoir, a key factor is the placement of the sample containing portion (the swab head) directly over the sonicating component as in FIG. 9. The PCB sensor board component of the overall cartridge must either have a cutout or otherwise not extend to the reservoir region in order to allow direct access of the sonicator unit to couple to the sample preparation reservoir. The bottom of the reservoir can also have a sonically conducting material that can form a soft seal with the sonic transmitting material directly over the piezo disc. This forms a continuous channel for the sonic energy to transmit into the reservoir from below all the way from the piezo disc.

The first phase of this sample preparation process is a high intensity sonication to achieve proper suspension of the reagents, particularly the beads in the reservoir such that these beads are available in solution to capture the target which is actively being eluted into the reservoirs solution with the aide of the sonication. An appropriate sonication piezo is a 1.6 mhz bending transducer piezo. The point is that it is not meant to generate cavitation and large shearing forces, but rather a gentle sonication, even at the high intensity phase.

Figure 10A:
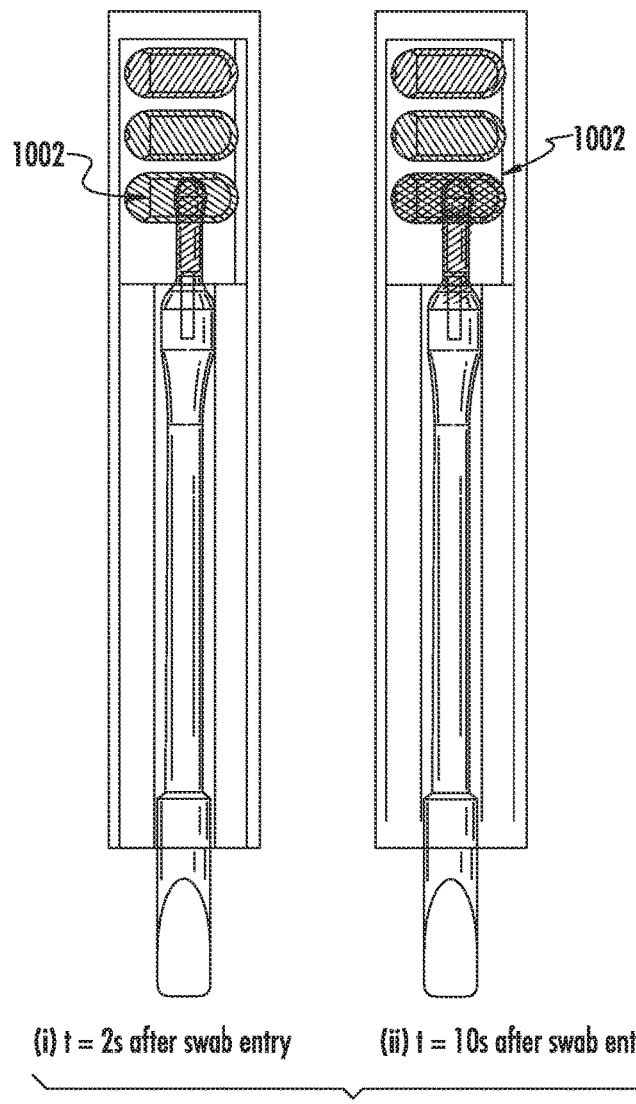
FIG. 10A depicts one embodiment of a sonicator at various times after swab entry.

Then the sonication is pulsed in order to keep the beads from settling and to continue to add energy into the system to enhance the hybridization between the affinity reagents on the bead and the target and the signaling antibody or nucleic acid for selective enzyme retention. Refer to FIGS. 10a and 11.

Figure 10B:
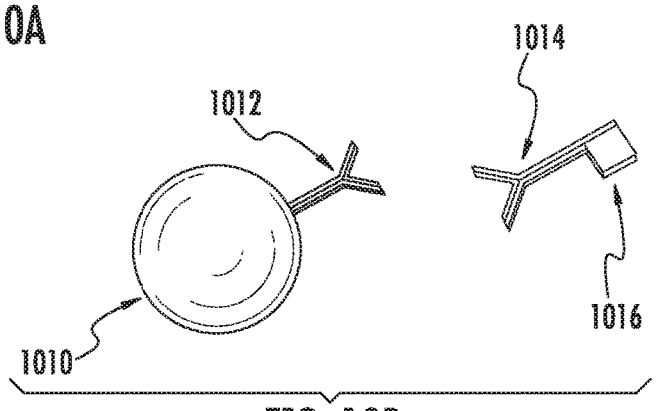
FIG. 10B schematically represents components present inside the reservoir.

As shown in FIG. 10A, after a few seconds, the sonicator helps to mix the sample with the reservoir's contents. FIG. 10A(i) shows the swab just after it is inserted. FIG. 10A(ii) shows the reservoir seconds after the sonication protocol is initiated. In FIG. 10A(i), the red dye from the swab is not mixed in the reservoir 1002; in FIG. 10A(ii), the red dye has mixed fully within the reservoir 1002. As represented in FIG. 10B, inside the depicted reservoir, we have a mixture containing millions of magnetic microbeads 1010 or nanoparticles possessing capture antibodies 1012 on their surface very specific to target proteins; these target proteins can be components on a viral membrane (for detection of viruses), proteins such as CRP, or even small molecules such as caffeine. Also cohabitating the reservoir is the signaling antibody 1014, which is conjugated to an enzyme 1016 called Horseradish Peroxidase (HRP) that can oxidize a chemical substrate (which means it strips it of an electron). This electron stripping can be measured on the electrochemical sensor and is proportional to the amount of target present. A more complete list of components is listed elsewhere herein.

FIG. 11A illustrates that in the reservoir 1100 there is a settled phase and an excited phase. In the settled phase, before sonication, beads are settled in the reservoir 1100. In the excited phase, during sonication, beads are mixing with the swab's payload (not pictured: the swab head). This allows for capture of target molecules.

The sonication profile, in other words, how long the piezo is on for and whether it is pulsed etc. varies according to the sample being tested. It is preferable that the system has fine grain control over these variables. In particular, for power consumption purposes, it is preferable that the piezo has an "on period" in which the piezo "pulses". In other words, for every 10 seconds the piezo is on for example 3 seconds and within that 3 seconds, the piezo turns on for 0.027 seconds and turns off for 0.027 seconds. These methods allow for the sample to not get too hot, to allow for hybridization, and to avoid consuming too much power, important in a battery operated system, while still providing the environment conducive to target capture and sandwich complex formation. See figure x for a screenshot of variable control over the piezo.

Another innovative feature of our system is the ability to update the sonication profile depending upon the cartridge and sample being tested. In other words, we utilize the remote updatability of the App, which communicates with the reader, to command and control the piezo such that it provides a different sonication profile depending upon the cartridge being added. Since more cartridges and tests are added to the system over time, and since all of the profiles don't have to be preloaded, it allows for much more flexibility in the system for handling new cartridges/tests.

Now that the beads have captured target (if present) and formed the sandwich complex, the system utilizes the liquid medium used for forming the complex as a transportation medium for getting the beads to the sensors by capillary flow of the whole solution past the sensor of choice.

The Method:
(1) the system opens a valve to allow the content of input/sample preparation reservoir (hitherto designated reservoir 1) to flow out using
(2) Microfluidics (capillary flow) to transport beads from reservoir 1 to the sensor, where a magnet underneath will localize these magnetic beads directly over the sensor.
(3) Then the system uses the same valving and flowing mechanism to wash away excess signaling enzyme not bound to any beads to remove nonspecific signal (wash solution is preferably in reservoir 3, most upstream)
(4) And then the system reuses the same valving and flowing mechanism to provide the chemical substrate the enzyme needs to create a net flow of electrons in proportion to the amount of target present (chemical substrate is preferably in reservoir 2, between reservoir 1 and 3.) This electron flow generated by oxidation/reduction chemistry is what we will measure on our electrochemical sensor.

The key here is to take the already formed sandwich complex bead (if target is present) and use the volume of liquid acting as a flow medium in a capillary channel to transport and passively deposit the beads onto the intended sensor.

The beads are magnetic, and therefore they are down from the transport solution to the surface of the sensor via magnetic force generated preferably through a permanent magnet located beneath the sensor (as part of the reader, not the cartridge), but this magnetic force can also be generated through electromagnetism from coils located on the sensor component of the cartridge.

Valve

This sections figures are FIGS. 13-15. The use of an inline production process of printed circuit boards to create a valve actuating element in a diagnostic product is described here. A via is a standard product of PCBs that is typically used for allowing signal traces on one layer of a PCB to continue electrically with another layer. The vias provide electrical continuity through multiple layers. Our system utilizes the fact that they are also excellent conductors of heat to a very precise location without affecting the areas around it because the material that comprises most PCBs, such as FR4 are excellent insulators of heat. This allows for minimal "crosstalk" between valves located close to each other.

The system utilizes these vias as point sources of heat to melt wax, preferably hydrophilic wax, that is holding back a volume of liquid. A resistive heating element generates the heat that is to be conducted to the exact location where the wax needs to be melted such that the reservoir has an opening to which its fluidic contents can drain through the opening into a microfluidic channel. This heating element can be on the board, as in serpentine trace in FIG. 15 (on the backside of the sensor component), or can be external to the cartridge board. In other words, the heating element can be located on the reader, but with spring loaded contacts to form an effective contact with the via, such that the via can conduct the heat to the wax barrier.

Therefore, the innovation has a heat conducting via created on the sensor component of the cartridge, a resistive heating element, a wax barrier, and a volume of liquid being held back. The wax forms a seal with the hole in the reservoir to prevent liquid from leaking into the microfluidic channel on the microfluidic component of the cartridge.

Current is allowed to flow through the resistive element, most likely through actuation of a transistor. Current passing through the resistive element generates heat through Joule heating. Because of physical contact between the resistive heater and the via, the heat is conducted through the via up to the wax barrier. Because of the heat, the wax barrier melts, allowing the liquid volume the wax was holding back to flow past the location of the former wax barrier.

To create the valve (not actuate during system operation):

It is preferable if the wax has the minimum height necessary to occlude the opening between 1) reservoir of liquid held back and 2) the microfluidic channel in order to minimize the distance heat must travel to melt the wax.

The preferred method for realizing this wax barrier is to apply melted wax to a heated via area such that the wax does not freeze upon contact with the via, which causes and unnecessary excess of height.

The valves are prepared by application of heat to the chip, especially the via area, such that the wax does not freeze on contact, which would cause an undesirable increase in height. Pancaking of the wax is preferable to minimize the height, which will maximize the chance of proper melting actuation of the valve. The heating is important because it allows for proper, regular, consistent formation of the valve.

The reservoirs preferably have an angled bottom such that dead volume is minimized. In other words, the area closest to the opening of the reservoir to the channel is at a lower height relative to the area of the reservoir further from the channel.

As shown in FIG. 13A, in the first reservoir 1301 occurs sample input and sample preparation; in the second reservoir 1302, is an enzyme substrate; and in the third reservoir 1303, is a wash solution. There is a valve opening 1304 at the base of each reservoir connecting to a microfluidic channel 1305. FIG. 13B shows a swab head 1350 in the first reservoir 1301.

Figure 14A:
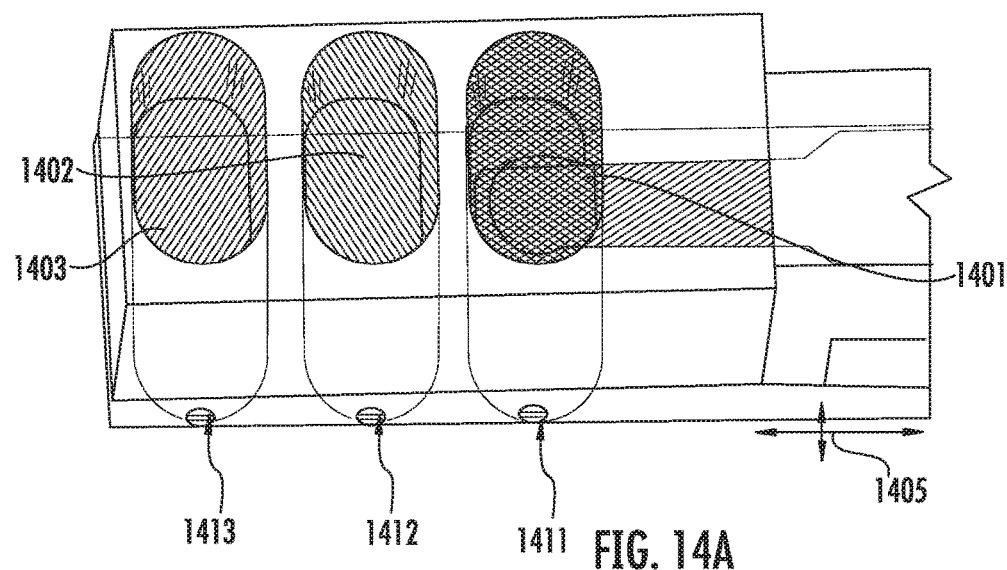
FIG. 14A-B depicts a portion of one embodiment of a cartridge, which includes valves, with a first valve closed and open, respectively.
Figure 14B:
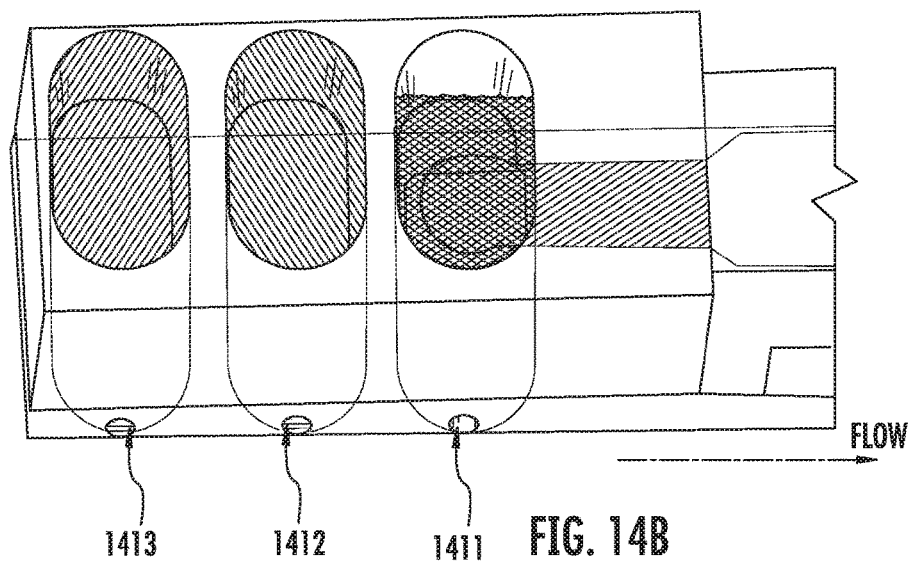

In FIG. 14, we use a phase change valve consisting of a hydrophilic wax with melting temperature around 50 degrees Celsius. A small amount of wax is deposited very precisely onto a via, which is continuous with a resistive heater on the bottom of the green sensor board (shown in FIG. 15). The via acts as a very precise shaft for delivery of heat directly to the location of the wax. This wax, in its solid state, seals the reservoir's opening that meets the microfluidic channel. When current is flowed through the resistive heater the via heats up the wax, melting it. The seal is broken, allowing liquid to flow out of the reservoir into the microfluidic channel. These valves are individually addressable and automated. Specifically represented in FIGS. 14A-B is a first reservoir 1401 for sample input and preparation, a second reservoir 1402 for enzyme substrate, and a third reservoir 1403 for wash solution. In FIG. 14A, the first valve 1411, the second valve 1412, and the third valve 1413 to the microfluidic channel 1405 are closed. In FIG. 14B, the first valve 1411 is open, and there is flow. The second valve 1412 and the third valve 1413 are closed.

Figure 15C:
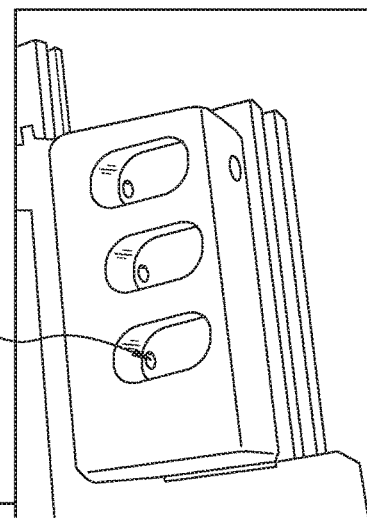
FIG. 15A-C depicts various views of one embodiment of a PCB component of a cartridge.
Figure 15B:
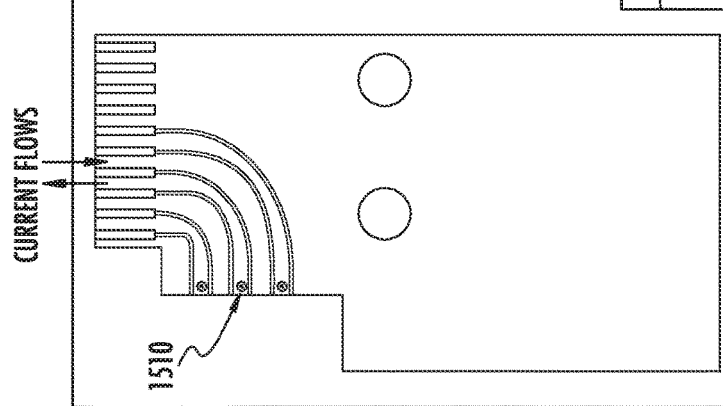
Figure 15A:
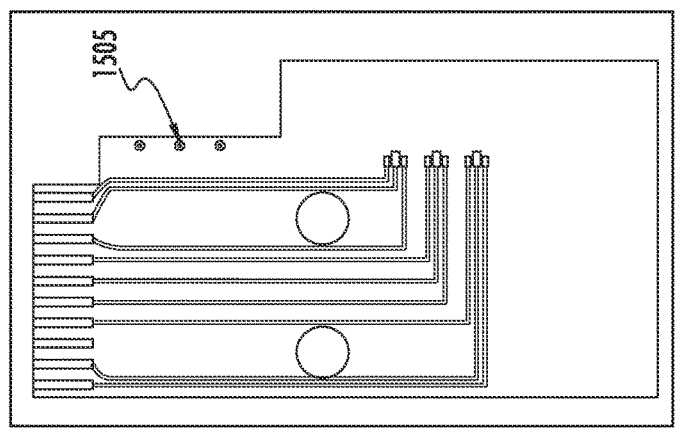

FIGS. 15A-C show the sensors and valve vias on the PCB sensor component of the cartridge. Specifically, FIG. 15A is a top view. The via 1505 delivers heat to the wax barrier. FIG. 15B is a backside view showing a resistive heater 1510 (formed by serpentine trace). FIG. 15C illustrates that an opening 1520 at the bottom of the reservoir meets the via, where wax is deposited to form a seal, preventing leakage of liquid into the microfluidic channel.

Flow

Figure 16:
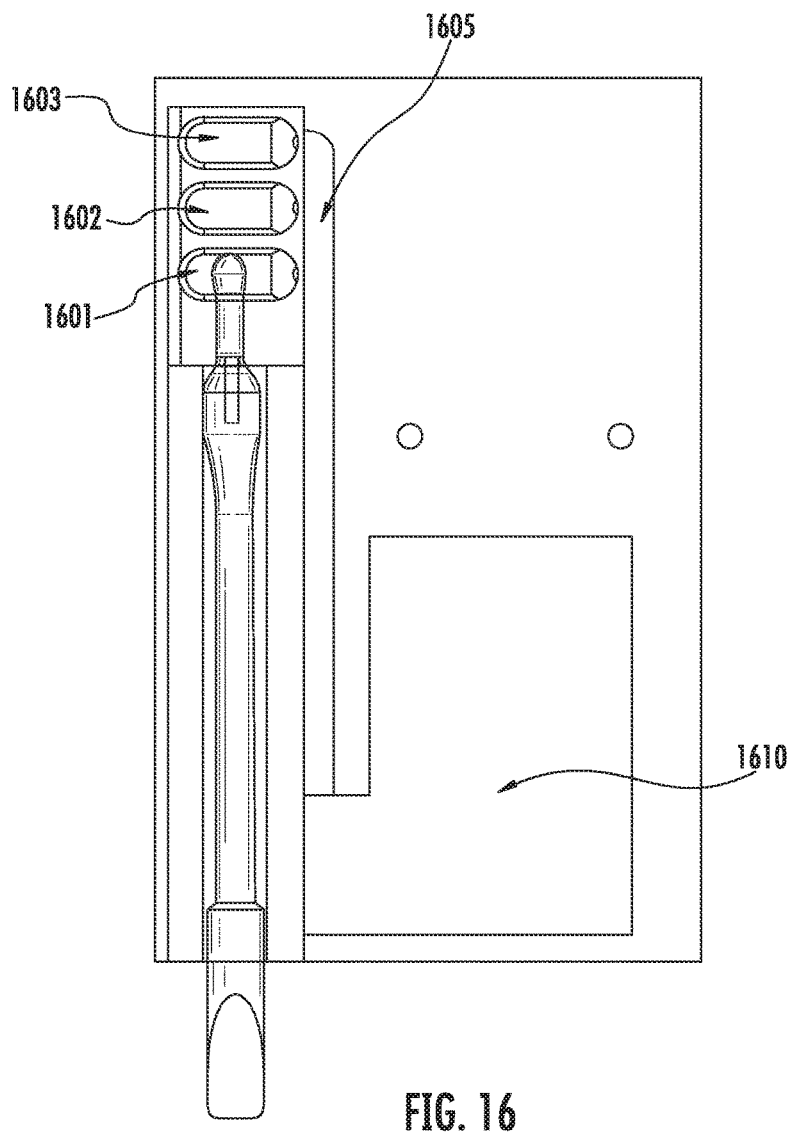
FIG. 16 depicts one embodiment of a microfluidic channel and reservoir component with one embodiment of a swab.

This section has reference FIGS. 16-21. In FIG. 16 there is shown a microfluidic and reservoir component with a swab. Depicted elements include: a first reservoir 1601 for sample input and sample preparation, a second reservoir 1602 with enzyme substrate, a third reservoir 1603 for wash solution, a microfluidic channel 1605, and an area for an absorbent pad 1610.

Upon completion of the sonication/preparation protocol, the liquid volume containing the beads becomes the transport vehicle for taking the beads from the preparation reservoir to the sensor for detection.

The liquid from the first reservoir 1601 flows downstream of the reservoir towards the sensors. There must be a vent downstream of the reservoir to allow displaced air to vent as the liquid flows into the channel 1605.

There must be a vent in the reservoir 1601 itself to allow for fluid flow (air) to replace the fluid (liquid) entering into the channel 1605. This can be formed by an air permeable PTFE membrane on the top of the reservoir component. The advantage of using PTFE is that it acts to seal off the reservoir from leakage out the top, yet allows for the liquid to drain out of the reservoir during flow of liquids from the reservoir through the microfluidic channel.

The hydrophilic channel is constructed by the sensor component of the cartridge making one of the walls and the microfluidic component of the cartridge makes up the other 3 walls of the channel. This channel can be made hydrophilic with the appropriate thermoplastic resin used to create the piece, or via surface modification, especially via pegylation (polyethylene glycol) grafting to the surface of the walls mediated by plasma treatment to activate the walls such that the PEG will bond, making a hydrophilic and protein resistant surface.

Additionally, a lateral flow type membrane, commercially available may be used such that the channels interior is not just empty space, but a wicking material.

The reservoirs are sequenced in a particular order. The sample preparation reservoir is the furthest downstream, closest to the sensors. The wash reservoir is furthest upstream. The chemical substrate reservoir for enzyme reaction is between sample preparation and wash reservoirs. The sample input reservoir is preferably first in order to accommodate the sample input and it must be upstream relative to the wash reservoir such that all enzyme not bound to the target carrying beads will be washed away and not create non-specific signal at the sensor. If the wash reservoir was downstream of the sample input, then unbound enzyme would get pinned against the upstream-most vent, causing non-specific signal to occur when the chemical substrate is released. This non-specific signal will drift downstream and be read by the sensors.

The valves are actuated in the sequence: sample preparation, wash, then chemical substrate. A certain amount of time is allotted for each valve to actuate, then flow time for the reservoir to empty it's components into the channel and be sucked up by the absorbent pad downstream of the sensors. Enough time for the absorbent pad to suck the channel dry such that very little to no fluid is left in the channel can be desirable such that very little mixing occurs between successive reservoirs contents.

At the end of the microfluidic channel there is an absorbent pad which wicks liquid from the microfluidic channel, downstream of the sensors. The volume the absorbent pad can wick must be enough to drain the sample reservoir and the wash reservoir, but only enough to pull the chemical substrate reservoir into the channel and over the sensors, then stop such that there is little to no flow over the sensors when enzyme bound to beads is turning over the chemical substrate to cause a detectable signal over the sensors where they are electrochemically "read".

The sample preparation volume of liquid transports the beads to the sensors where they are caught via magnetic force over a sensor for detection. The channel is washed and chemical substrate is provided for any enzyme bound to beads.

Figure 17C:
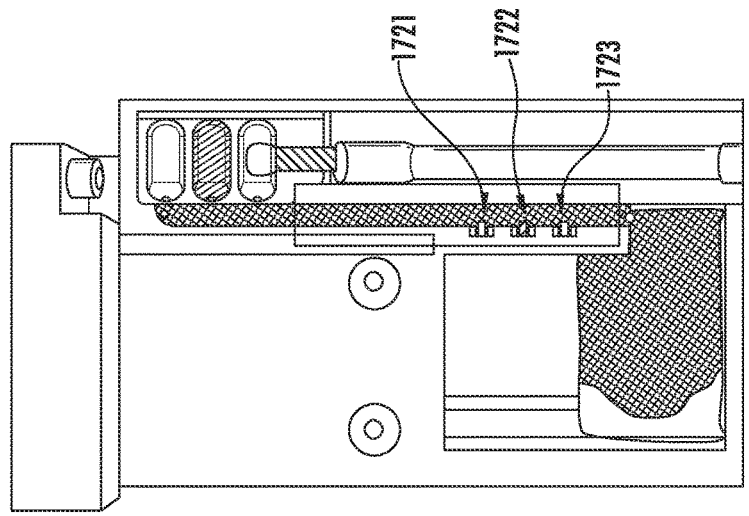
FIG. 17A-C depict the progression of flow in one embodiment.
Figure 17B:
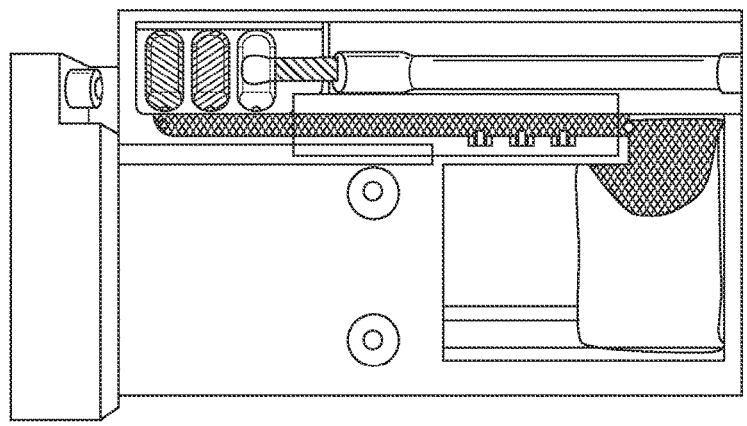
Figure 17A:
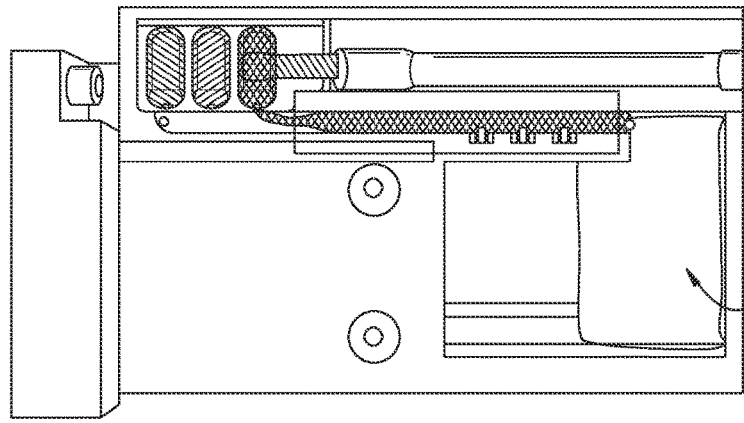
Figure 18:
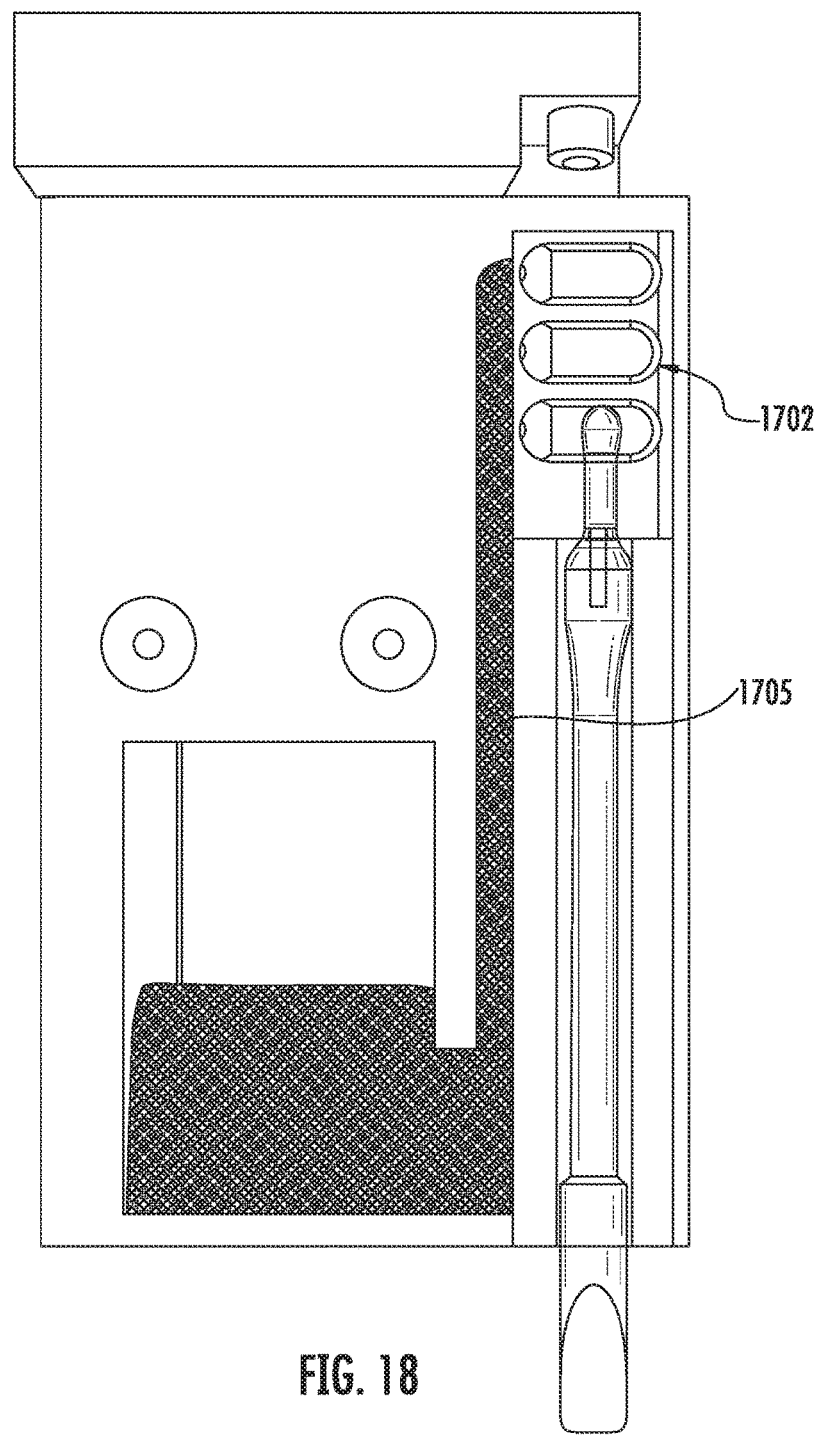
FIG. 18 depicts completed flow in one embodiment.

An example of flow to transport beads to sensor is provided in FIGS. 17A-C and 18. FIG. 17A shows flow 2 seconds after valve burst; FIG. 17B shows flow 4 seconds after valve burst, and FIG. 17C shows flow 12 seconds after valve burst. In FIG. 17A, when the sonication protocol is complete, the valve for the first reservoir is actuated and the contents flow into the main microfluidic channel. In FIG. 17B, the absorbent pad 1710 draws the liquid completely out of the reservoir. The magnetic beads are localized over sensor 1722 (which has a magnet located underneath). In FIG. 17C, the reservoir is emptied, and now we will wash the channel with the volume of liquid contained in the third reservoir (clear liquid). Notice that sensor 1722 is darker than sensors 1721 and 1723 because of bead localization. As shown, an ambient noise sensor can also act as a control to determine the test was performed correctly. Sensors 1701 and 1703 are used to subtract out ambient electrochemical noise. In FIG. 18, the flow is complete. The microfluidic channel 1705 is filled with enzyme substrate from reservoir 1702. The channel 1705 has now been washed with the contents of the third reservoir (empty); the chemical substrate from the second reservoir 1702 (empty) needed by the signaling enzyme is now in the channel. Detection can now take place.

Bubbles are often a problem in microfluidic systems. To counter this issue, at least some of the top of the microfluidic channel (on the microfluidic component of the cartridge) is replaced with PTFE membrane such that the PTFE forms the "ceiling" of much of the channel (as in FIG. 20). This allows for passive degassing of bubbles contained within the channel. The pore sizes of the PTFE membrane can vary and include anything from 0.1 microns to 3 micron pores and the membrane can be sealed onto the channel with adhesive.

Figure 19:
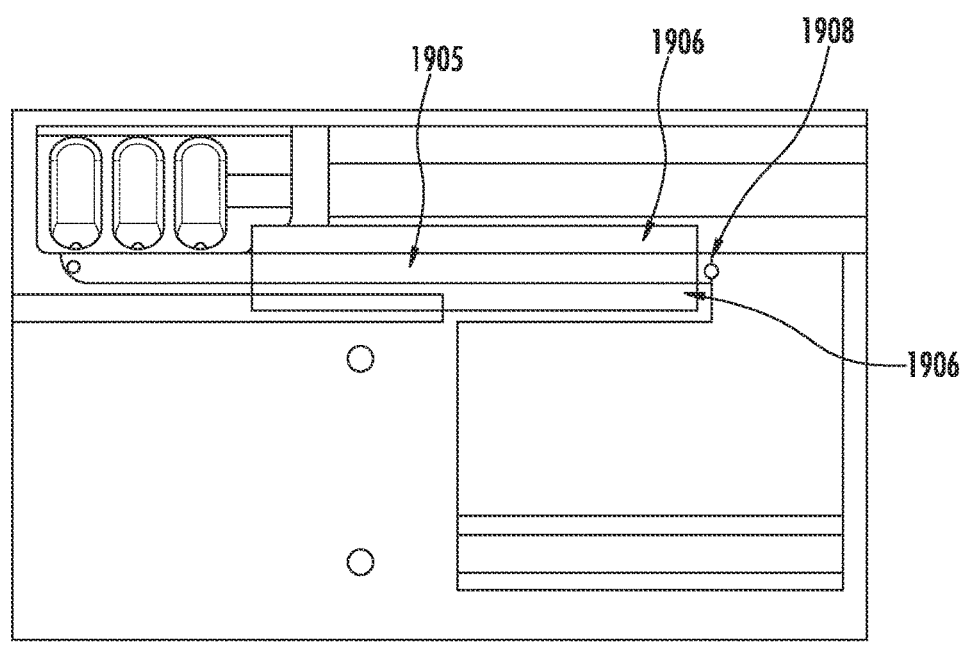
FIG. 19 depicts a top view of one embodiment of the microfluidic channel and reservoir component.

FIG. 19 shows an example in which the top of the channel 1905 in the microfluidic component is cut out. A lip 1906 on both sides of the channel 1905 allows for bonding of PTFE membrane on top of the channel 1905. A vent 1908 is also provided. In FIG. 20A, it is again visible that the top of the channel 1905 is cut out. Also visible is the PTFE membrane 2000 (wide enough to bond to lip on both sides of the channel 1905). In FIG. 20B, the PTFE membrane 2000 is in place and bonded to form a microfluidic channel top for passive degassing of bubbles.

Because PTFE is hydrophobic, prewetting is generally required for liquid to flow properly along the PTFE membrane. To prevent a distinct prewetting step, as opposed to just flowing the sample preparation reservoirs contents into the channel, a "structural prewetting" can be accomplished.

What is meant by structural prewetting is that rails of hydrophilic material can run the length of the PTFE membrane promoting flow of liquid along the rails to facilitate the first reservoirs liquid to flow in the microfluidic channel. The hydrophilic rails help overcome the hydrophobic resistance of the PTFE. These rails can be formed in a multitude of ways that include thin plastic rails that span the length of the area where the PTFE acts as the ceiling of the channel. In other words, the PTFE will be covering the rails as it acts as the microfluidic channel's ceiling. Additionally, adhesives directly on the PTFE can form the rail, or a patterned surface modification of the PTFE membrane such that the surface modification for hydrophilicity run the length of the channel.

Detection

The electrochemical sensors where detection takes place are preferably made through ENIG process and thus have gold on the surface. There are three electrodes, a working, counter, and reference electrode. Each have a surface chemistry formed onto them. This has thiolated ethylene glycol, preferably a dithiol such as hexaethylene glycol dithiol for added stability. The hydrophilic nature of the head groups facilitates flow and protein resistance. The surface is preferably backfilled with mercaptoundecanoic acid, Another potential backfiller is mercaptohexanol. The layer is formed by sequential addition and incubation of first the ethylene glycol dithiol and then backfiller at unelevated temperatures.

Notably, the method does not require affinity reagents at the sensors themselves, which enhances the overall speed of the system.

Besides the target sensor, it is desirable to have an ambient electrochemical noise sensor which detects background noise in the system from non-specifically bound enzyme. This background noise sensor will then be used to help subtract out system noise from the signal generated at the target sensor.

As an example, as shown in the photograph and zoomed in schematic representation in FIG. 21, sensor 2102 has millions of microbeads localized over it. Excess HRP signaling enzyme has been washed away and chemical substrate for the HRP is the only liquid remaining in the microfluidic channel. Note that while the beads are depicted as suspended over the sensor, in reality the magnet will localize the beads against the surface of the sensor, not in suspension above it. The enzyme substrate solution is in the channel containing Tetramethylbenzidine molecules (from the second reservoir) and hydrogen peroxide; both are necessary for signaling enzyme to operate to create a current flow in proportion to presence of target. As shown, the working electrode 2104 of sensor 2102 has surface chemistry 2106: a carefully designed self-assembled monolayer reduces non-specific signal generation from enzyme sticking and smooths over defects on gold surface, leading to much more reproducible results.

Figure 23:
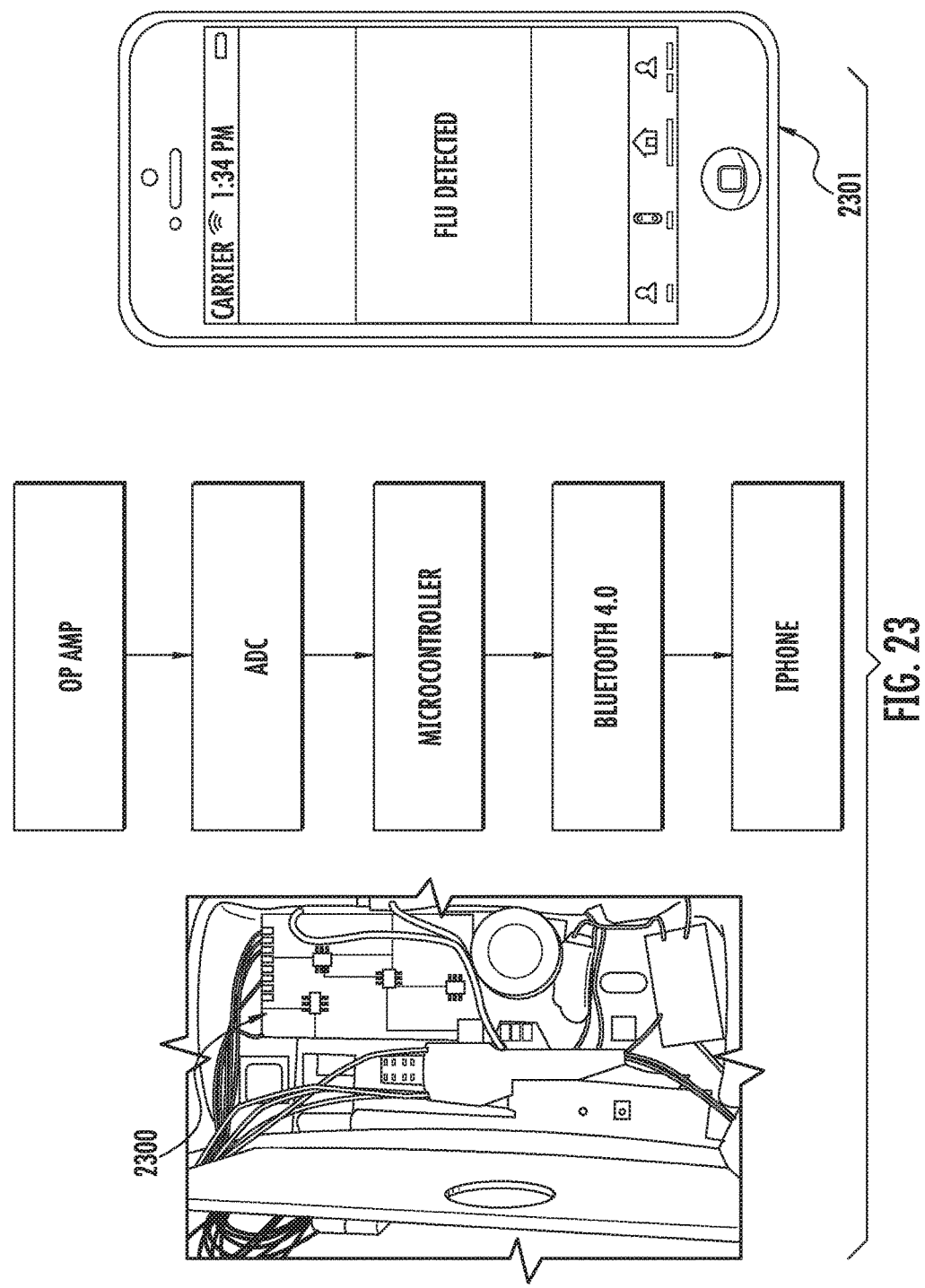
FIG. 23 illustrates the internal components of a one embodiment of a reader, including an electrochemical circuit; a block diagram of the electrochemical circuit components is also provided.

The detection is preferably carried out using standard electrochemical circuit that utilizes a bias potential generated at the reference electrode such that the oxidation/reduction reaction can proceed. The potential is held at the reduction potential of the chemical substrate (low enough that there is little nonspecific reduction of reducible species in the solution) such that the flow of electrons to the oxidized molecules can be quantified using a current to voltage op amp connected to the working electrode. For example a common substrate, tetramethylbenzidine is used for HRP. When present, HRP oxidizes TMB molecules, and these molecules are in turn reduced by the working electrode. Since this event occurs in proportion to the amount of HRP present, we see a change in the current to voltage op amp that is measured by the analog-to-digital converter, which we can then take as the actual signal to be interpreted by the microcontroller as depicted in FIG. 23. As further shown in FIG. 23, the electrochemical circuit 2300 (shown amongst the reader internals) converts the current sensed at the working electrode to a voltage using a current-to-voltage op amp scheme. This analog signal is routed to an Analog-to-Digital-Converter (ADC) on the microcontroller in the reader. From there, the signal is transmitted via Bluetooth 4.0 to the iPhone 2301, where the result is interpreted and displayed.

Figure 24:
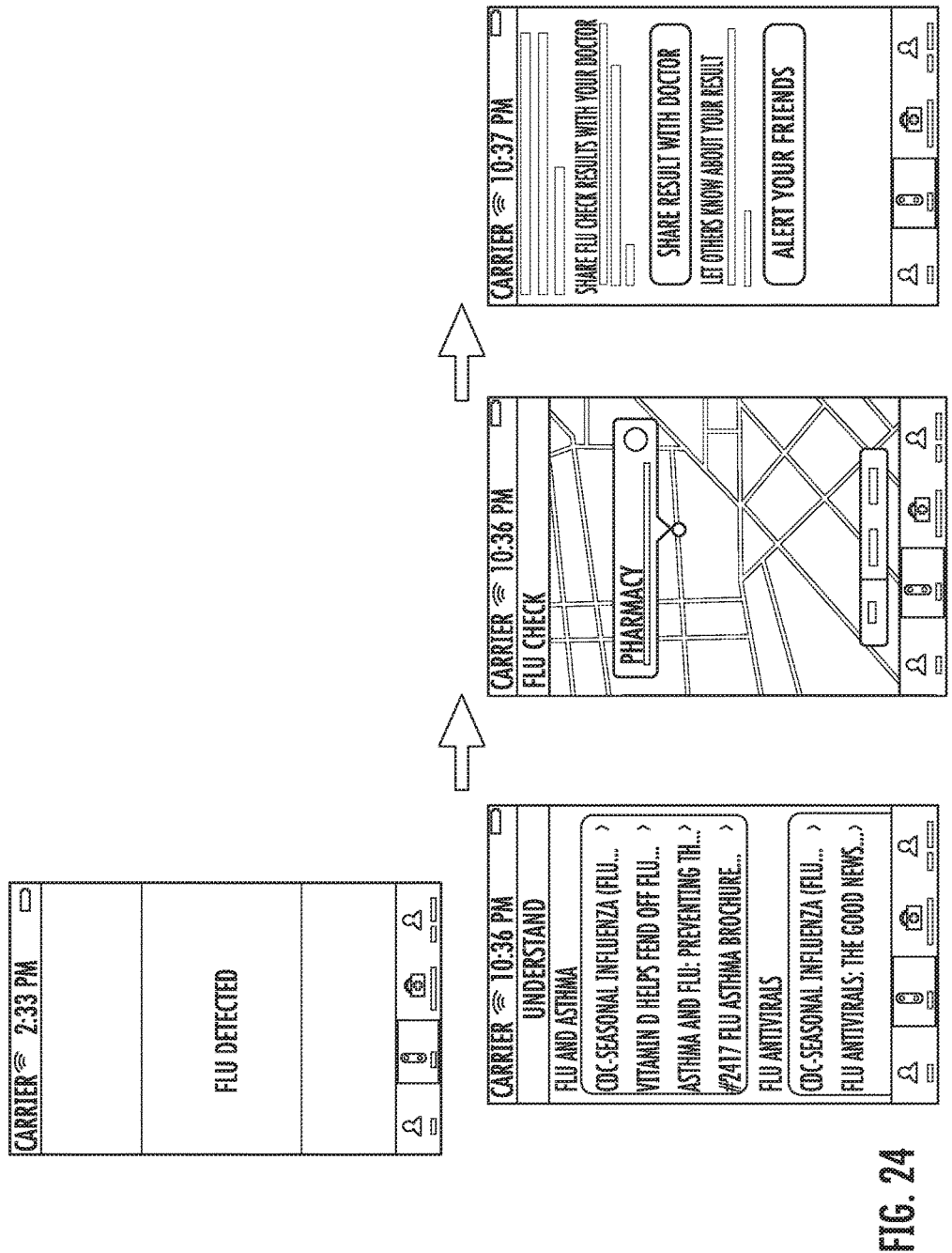
FIG. 24 depicts various views of one embodiment of an App.

An example of the App display is provided in FIG. 24; in the example, flu was detected. The App provides customized information based on personal medical history entered earlier (asthma for instance). Antivirals are a strong option for treating flu and recommended by the CDC. You can set pharmacy information in the app and transmit result to doctor with pharmacy phone number. You can let others in your network know (for instance other mothers at your daycare via Facebook).

Figure 22B:
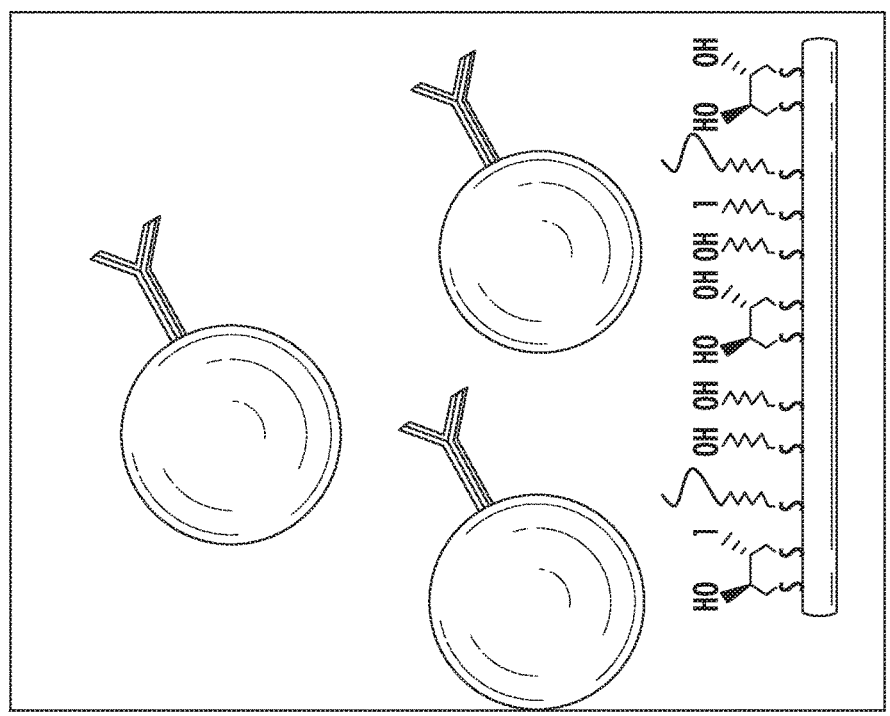
FIG. 22A-B provides schematic representations of one embodiment of the surface chemistry; one embodiment of microbeads are also schematically represented with and without a coupled target.
Figure 22A:
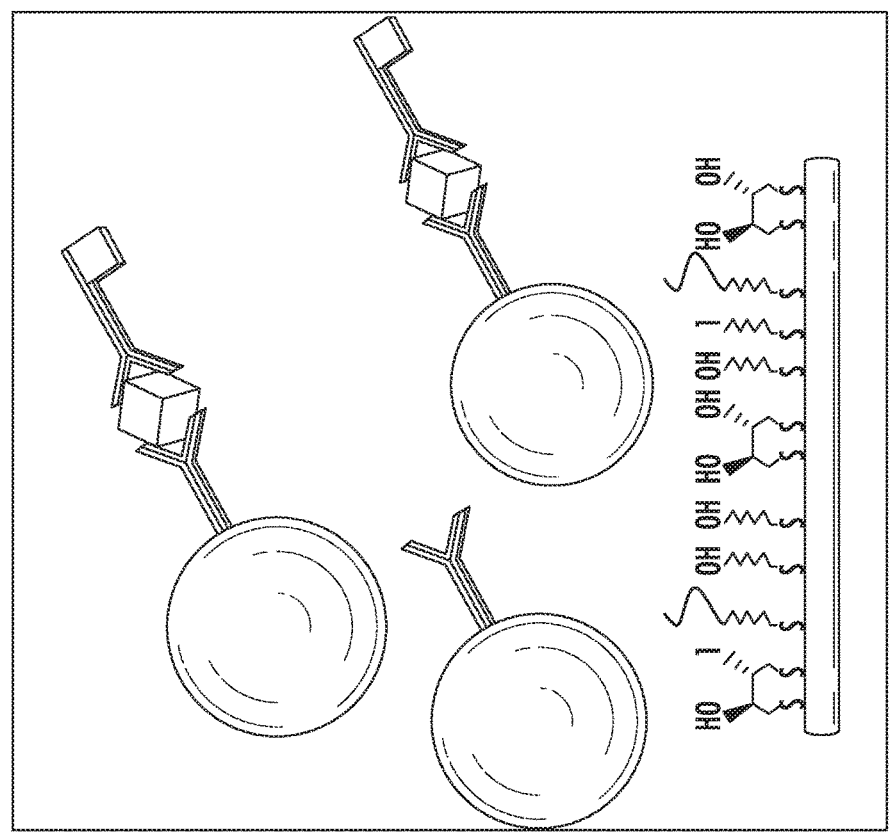

HRP or other signaling enzyme is present over the sensor in proportion to the amount of target captured because of the formation of the sandwich complex to which it is a part and which can only be formed in the presence of target. Refer to FIG. 22. Specifically, FIG. 22A shows the working electrode with target present, and FIG. 22B shows the working electrode without the target. With the target: HRP, the signaling enzyme, will oxidize the TMB molecules in the solution (from the second reservoir), causing a net flow of electrons into the cell. This flow of electrons is measured by the electrochemical circuitry. The amount of signal is proportional to the amount of signaling enzyme, which is proportional to the amount of target. This gives us a quantitative result concerning the amount of target captured. Without the target: there is not signaling enzyme to oxidize TMB, thereby little to no flow of electrons into the cell. The surface chemistry is critical for preventing HRP signaling enzyme from sticking to the gold sensors and producing non-specific signal.

The bottom of the cartridge has a cutout that allows for the permanent magnets to be closer to the sensors as the cartridge slides in. The cutout allow the cartridge to slide in without hitting the permanent magnets. The closer the permanent magnets are to the sensor, the more force they are able to exert, meaning that smaller magnets are capable of exerting equivalent magnetic field strengths to larger magnets which are more costly. Refer to FIG. 5. Additionally, smaller magnetic fields can limit the amount of cross talk between magnets under different sensors, which is important in a multiplexed assay, which is discussed in the Multiplexing section.

Multiplexing

A few innovative methods for achieving multiplexing are discussed. They all begin with the same initial premise: that initially multiple populations of beads exist in the first reservoir.

A population of beads is defined by having two differentiating characteristics:

1) affinity to a certain set of targets (through capture antibody, capture DNA probe, or other affinity molecule on the surface of the bead)

2) a difference in size, magnetic response, density, or any combination thereof

No two population of beads can have the same affinity (1) or same differentiating physical characteristic to be exploited for separation (2).

The beads are utilized to capture the targets as in the methods earlier described. The key point is that a distinguishing physical characteristic between bead populations allows for the differentiated querying of target acquisition (see detection section) since different populations of beads have different target sets.

Method 1, Dead-End Filtration Through a Series of Size Exclusion Filters:

This method relies on differentiation of bead size. Dead-end filtration is a commonly used term for filtering through a membrane. In this method we utilize the same principle in an innovative way in order to achieve a multiplexed and quantitative interrogation of multiple sized beads. As the beads flow out of the reservoir and into microfluidic channel, we have a sequence of filters in order of largest pore size filter first. Each filter is placed in close proximity to an electrochemical sensor that is designated to read that population of beads. Beads of smaller size than pore size will pass through the filter with the flow of liquid down the channel. Beads larger than the pore size will remain behind, in close proximity to the sensor designated to read its signature. Through successive filters, the bead populations in order of larger to smaller are trapped over the sensors designated to read them. In this manner, different populations of beads with different target sets are then queried in the manner we have described earlier in the detection section.

This process can be enhanced through use of magnetism. Beads of same material composition vary in their magnetic response with the square of the diameter of the bead. Therefore, a magnetic field will interact differentially on beads of different size allowing a sorting mechanism to take place.

There are two ways this differential magnetic response can be exploited to enhance separation speed and specificity. As the beads leave the reservoir a magnetic field (generated through an electromagnetic force, or preferably through a permanent magnet) applied to the channel can be used to "order" the beads. What is meant by order is that since larger beads will feel the magnetic force more strongly than smaller beads, they will move more slowly downstream than the smaller beads, resulting in a preference for smaller beads to progress down the channel earlier than larger beads, which can decrease likelihood of bead-based clogging of pores. Bead clogging of a pore would decrease multiplexing specificity and could prevent proper testing altogether by restricting the flow of liquid needed to wash away excess enzyme and provide chemical substrate for the captured enzymes to work. It is critical to tune the velocity of the flow and the magnetic strength such that the larger beads aren't captured by the magnet, preventing them flowing to their destination sensor.

Method 2: Successively Stronger Magnetic Force for Membraneless Separation:

Ideally, no membrane would be utilized because of the effect it has on flow rates, cost of membrane and cost of integrating membrane into cartridge. Therefore a membraneless separation technology is of extreme value.

By exploiting the same mechanism described earlier about the magnetic force response of a bead scaling with the square of the diameter of the bead, we can achieve this separation of bead populations in a single channel by employing magnetic fields of successively stronger force in the flow in close proximity to a destination sensor for each bead population. In other words, instead of a series of membranes in proximity to a destination sensor, we have a series of magnetic fields (preferably set up with permanent magnets located underneath the cartridge and built into the reader) such that the largest magnetic beads are localized at the first sensor because they are unable to escape the first magnetic field, which is just strong enough to capture the largest beads, but not strong enough to capture the second largest set of beads (or any other set of beads). Bead populations with smaller diameters than the population with the largest beads will move on downstream with the flow of liquid until they are caught by the magnetic field located at their intended destination sensor. The second weakest magnetic field will capture the population of beads with the second largest diameter. The bead population with the third largest diameters will be captured by the third smallest magnetic fields and so on. The smallest magnetic beads are caught by the strongest magnetic field. Thereby each bead population is localized to a destination sensor and the detection proceeds as described earlier. The magnetic force will keep the beads in place during the washing and chemical substrate addition phase of the test.

The reference figures are FIGS. 25-26. The top view of FIG. 25A depicts magnets (e.g., magnet 2534), sensor 2511, sensor 2512, sensor 2513, sensor 2514, a microfluidic channel 2505, reservoirs 2501, and an absorbent pad area 2520. The side view of FIG. 25B depicts a magnet 2531 underneath sensor 2511, a magnet 2532 underneath sensor 2512, a magnet 2533 underneath sensor 2513, and a magnet 2534 underneath sensor 2514. Permanent magnets immobilized in the reader (depicted as circles in top view and cylinders in side view) are order successively such that further downstream of the reservoirs towards the absorbent pad, the magnetic field felt by particles flowing in the microfluidic channel gets stronger because the magnet is located at successively closer to the sensors. This allows for the largest particles (or population of beads) to become magnetically localized on the sensor closest to the reservoirs (sensor 2513) while the smallest particles are localized on the sensor furthest downstream (sensor 2514). The second largest set of particles end up on sensor 2512 and third largest set of particles on sensor 2513.

In FIG. 26, a side view of the cartridge shows a magnet 2631 underneath sensor 2611, a magnet 2632 underneath sensor 2612, a magnet 2633 underneath sensor 2613, and a magnet 2634 underneath sensor 2614.

Method 3: Cross-Flow Filtration Utilizing Magnetic Fields and Membranes:

Most cross flow filtration technology uses flow down a channel plus pressure and membranes perpendicular to the flow of liquid to prevent membrane fouling common with dead-end filtration. Liquid and particles smaller than the membrane cut off size are pushed through the membrane into another fluid channel.

The method described here uses magnetic force, instead of pressure, in order to exert the force perpendicular (or any proper angle not directly parallel to the flow) to the flow such that magnetic beads below a certain diameter are able to move through a membrane with pore size larger than its diameter towards a sensor where they will be localized through magnetic force and held during the washing and detection steps as described earlier.

This method is facilitated by use of an "aligning" or "focusing" magnet upstream of the membranes such that the magnetic beads are pulled to the side of the channel where the membranes are located such that they have the opportunity to feel the magnetic field acting to pull beads of the right size through the membrane.

In this method, membranes with smallest pore size are most upstream and progressively membranes with larger pore size are downstream. Otherwise, all beads smaller than the cut off would enter into the sensor region reserved for the largest of beads.

Just as in standard crossflow filtration techniques, the two most critical parameters are flow velocity and transmembrane pressure (or magnetic force in our case).

Multiple filters of the same size can be added one after another in order to collect all beads of the proper size and it is preferable that all of these off shoot channels collect over a single sensor but it is not necessary.

Production of a Multiplexed Cartridge

To apply a local magnetic field in a precise manner will require a special cutout of the cartridge bottom such that permanent magnets affixed to the reader will be able to slide into place where there magnetic field will precisely affect the beads.

Implementing the membrane placement within the cartridge during production requires some innovative methods. We propose a processing step such that the membrane is cut and adhesive applied such that the bottom (the floor of the channel) side is taped down during assembly to the PCB sensor board. A series of vents are used such that vacuum can be applied which will raise up the membrane such that they can form an adhesive seal against a frame on the main channel wall where the membrane will form its angled off shoot for beads smaller than the membrane pore size.

In effect, the membrane will be sucked into place and bonded through applied vacuum and adhesive onto the main channel's egress into the side channel. Membranes taped flat at the off shoots (not in the main channel) will be tombstoned up into place on the frame of the entrance to the side channel with applied vacuum.

Built into the cartridge are these frames, which are small protrusions from the ceilings at the entrance to the side channels (offshoots).

Additionally, this principle can be applied to the dead-end filtration method. Frames are built into the main channel, rather than the side channel, and vacuum is applied between each set of membranes and before the first to tombstone the membranes into place.

Although the foregoing has included detailed descriptions of some embodiments by way of illustration and example, it will be readily apparent to those of ordinary skill in the art in light of the teachings of these embodiments that modifications may be made without departing from the spirit or scope of the appended claims.

What is claimed is:

1. A system for identifying the presence, absence, and/or quantity of a molecule of interest in a sample, comprising:
   a reader; and
   a cartridge that fits into the reader, the cartridge configured to accept a sample collection device that fits into the cartridge,
   wherein the cartridge comprises:
      a first reservoir for storing a liquid, wherein a mixture comprising the liquid and the sample is formed in the first reservoir when the sample collected by the sample collection device is inserted into the first reservoir, and wherein the mixture further comprises a plurality of magnetic particle complexes;
      a second reservoir for storing a chemical substrate;
      an analysis channel comprising an electrochemical sensor; and
      valve-actuating elements for transferring the mixture from the reservoir directly into the analysis channel and the chemical substrate from the second reservoir directly into the analysis channel, wherein the mixture localized over the electrochemical sensor reacts with the chemical substrate at the electrochemical sensor in the analysis channel for detection by the electrochemical sensor, and
   wherein the reader comprises a permanent magnet adjacent to the analysis channel when the cartridge fits into the reader such that the plurality of magnetic particle complexes can be localized in the analysis channel at the electrochemical sensor within a magnetic field generated by the permanent magnet.

2. The system of claim 1, wherein each of the plurality of magnetic particle complexes comprises a magnetic particle.

3. The system of claim 1, wherein the permanent magnet comprises more than one magnet.

4. The system of claim 1, wherein the electrochemical sensor releases a flow of electrons in a quantity proportional to a number of the plurality of magnetic particle complexes localized at the electrochemical sensor in the analysis channel in response to reactions between the mixture and the chemical substrate.

5. The system of claim 1, wherein the molecule of interest comprises one or more of a nucleic acid, protein, or small molecule.

6. The system of claim 1, wherein the reaction detected by the electrochemical sensor is proportional to a number of signaling enzymes of the plurality of magnetic particle complexes localized over the electrochemical sensor in the analysis channel.

7. The system of claim 6, wherein the second reservoir is configured to store a liquid comprising the chemical substrate, and wherein the chemical substrate is configured to react with the signaling enzymes.

8. The system of claim 1, wherein the cartridge comprises a slot to allow for the permanent magnet to slide into place underneath the electrochemical sensor.

9. The system of claim 1, wherein the reader is configured to send or receive, or both, signals to a mobile device indicative of a test result.

10. The system of claim 9, further comprising an application stored on the mobile device, the application configured to cause the mobile device to display the test result.

11. The system of claim 1, wherein the reader is configured to send or receive, or both, signals to a mobile device indicative of a test protocol.

12. The system of claim 1, wherein the cartridge further comprises a first valve between the first reservoir and the analysis channel and a second valve between the second reservoir and the analysis channel.

13. The system of claim 12, wherein the first and second valves are phase change valves.

14. The system of claim 13, wherein the valve-actuating elements comprise vias configured to heat the phase change valves to transfer the mixture and the chemical substrate to the analysis channel.

15. The system of claim 1, further comprising a sonicator configured to direct energy into the mixture in the first reservoir.

16. The system of claim 1, further comprising a third reservoir for storing a wash solution, wherein one of the valve-actuating elements facilitates transfer of the wash solution to the analysis channel.

17. The system of claim 1, wherein the system further comprises the sample collection device, the sample collection device configured to collect the sample from blood, urine, or saliva.

* * * * *